(12) United States Patent
Comlay et al.

(10) Patent No.: US 7,608,604 B2
(45) Date of Patent: Oct. 27, 2009

(54) ANTIPARASITIC AGENTS

(75) Inventors: Stuart Nicholas Comlay, Sandwich (GB); Joanne Clare Hannam, Sandwich (GB); William Howson, Sandwich (GB); Christelle Lauret, Sandwich (GB); Yogesh Anil Sabnis, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 12/028,192

(22) Filed: Feb. 8, 2008

(65) Prior Publication Data

US 2008/0194694 A1 Aug. 14, 2008

Related U.S. Application Data

(60) Provisional application No. 60/946,820, filed on Jun. 28, 2007, provisional application No. 60/889,041, filed on Feb. 9, 2007.

(51) Int. Cl.
*A61K 31/26* (2006.01)
*C07C 255/01* (2006.01)

(52) U.S. Cl. ...................... 514/112; 558/303
(58) Field of Classification Search ................. 558/303; 514/112
See application file for complete search history.

(56) References Cited

FOREIGN PATENT DOCUMENTS

| EP | 0 953 565 | 3/1999 |
|---|---|---|
| WO | 02/49641 | 6/2002 |
| WO | 02/50052 | 6/2002 |
| WO | 02/060257 | 8/2002 |
| WO | 2005/044784 | 5/2005 |
| WO | 2005/121075 | 12/2005 |
| WO | 2006/043654 | 4/2006 |
| WO | 2006/134466 | 12/2006 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
"Tautomer." Retrieved via the Internet [Dec. 11, 2008], URL: http://en.wikipedia.org/wiki/Tautomer.*
Berkowitz, David B. Use of fluorinated functionality in enzyme inhibitor development: Mechanistic and analytical advantages. Journal of Fluorine Chemistry 129 (2008) 731-742.*
Patani, George A. Bioisosterism: A rational Approach in Drug Design. Chem. Rev. 96 (1996) 3147-3176.*
PCT International Search Report, PCT/IB2008/000250.
Welch and Lim, "The synthesis and biological activity of pentafluorosulfanyl analogs of fluoxetine, fenfluramine, and norfenfluramine", Bioorganic & Medicinal Chemistry, 15:6659-6666, 2007.

* cited by examiner

*Primary Examiner*—Kamal A Saeed
*Assistant Examiner*—Samantha L Shterengarts
(74) *Attorney, Agent, or Firm*—Martha A. Gammill

(57) ABSTRACT

The present invention relates to compounds of the formula (I)

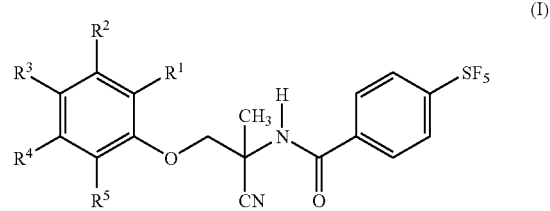

or a tautomer or prodrug thereof, or a pharmaceutically acceptable salt of said compound, tautomer or prodrug, wherein:
$R^1$, $R^2$, $R^3$, $R^4$ and $R^5$ are each independently selected from H, halo, CN, $CF_3$ and $CONH_2$; compositions containing such compounds and the uses of such compounds as antiparasitic agents.

12 Claims, No Drawings

ANTIPARASITIC AGENTS

CROSS-REFERENCE TO RELATED APPLICATIONS

This application claims the benefit of priority to U.S. Provisional Application No. 60/889,041 filed Feb. 9, 2007, and U.S. Provisional Application No. 60/946,820 filed Jun. 28, 2007.

BACKGROUND OF THE INVENTION

The present invention relates to pentafluorothiobenzamidoacetonitrile derivatives. The invention also relates to pharmaceutical compositions containing such compounds and their use in treating parasitic infestations.

There is a continuing need to provide new agents for the control of parasitic infestations that present a threat to human and animal health. In particular, new agents are needed to manage endoparasitic infestations in livestock animals due to the increasing prevalence of parasites, and in particular nematodes, that are resistant to many of the agents currently approved for this indication.

European patent application EP-0953565-A2 (Nihon Nohyaku Co. Ltd.) describes a genus of amidoacetonitrile derivatives and reports that these compounds have insecticidal properties. International patent application WO-2002/060257-A1 (Novartis AG) records that the same genus is active against endoparasites such as helminths. Related genera and subgenera are discussed in WO-2002/049641-A2 (Novartis), WO-20021050052-A1 (Syngenta), WO-2005/044784-A1 (Novartis), WO-2005/121075-A1 (Novartis) and WO-2006/043654 (Nihon). The mechanism by which these agents act has not yet been fully elucidated.

There remains a need for further compounds as alternative or improved therapeutic agents. Preferred compounds should be potent parasiticidal agents while presenting little or no toxicity to the host animal, and should exist in a physical form that is stable, non-hygroscopic and easily formulated. They should have high bioavailability, be metabolically stable and possess favourable pharmacokinetic properties. When intended for use in livestock animals, the compounds should be cleared in such a manner as to minimise withholding times without presenting a risk to the food chain.

SUMMARY OF THE INVENTION

In a first aspect, the present invention provides a compound of the formula

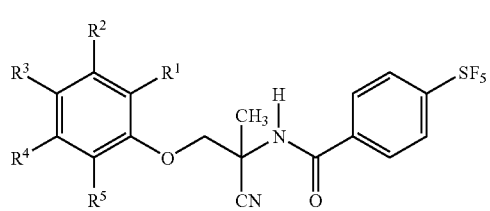

(I)

or a tautomer or prodrug thereof, or a pharmaceutically acceptable salt of said compound, tautomer or prodrug, wherein:

$R^1$, $R^2$, $R^3$, $R^4$ and $R^5$ are each independently selected from H, halo, CN, $CF_3$ and $CONH_2$.

In a further aspect, the present invention provides a compound of the formula (I) or a tautomer or prodrug thereof, or a pharmaceutically acceptable salt of said compound, tautomer or prodrug, for use as a medicament.

In a further aspect, the present invention provides for the use of a compound of the formula (I) or a tautomer or prodrug thereof, or a pharmaceutically acceptable salt of said compound, tautomer or prodrug, for the preparation of a medicament for the treatment of a parasitic infestation in a host animal.

In a further aspect, the present invention provides for a method of treatment of a parasitic infestation in a host animal, comprising treating the host animal with an effective amount of a compound of the formula (I) or a tautomer or prodrug thereof, or a pharmaceutically acceptable salt of said compound, tautomer or prodrug.

In a further aspect, the present invention provides a pharmaceutical composition comprising a compound of the formula (I) or a tautomer or prodrug thereof, or a pharmaceutically acceptable salt of said compound, tautomer or prodrug, and a pharmaceutically acceptable carrier.

DETAILED DESCRIPTION OF THE INVENTION

For the purposes of the present document, the following definitions apply:

"Halo" includes fluoro, chloro, bromo or iodo.

The term "pharmaceutically acceptable" as used in this specification, for example with reference to salts and solvates, includes "veterinarily acceptable" and "agriculturally acceptable".

The compounds of formula (I) have an asymmetric carbon atom (chiral centre), labelled 1* in the structural formula below. Accordingly, the compounds of formula (I) may exist as optical isomers. The present invention includes individual enantiomers of the compounds of formula (I) and mixtures thereof, including racemates.

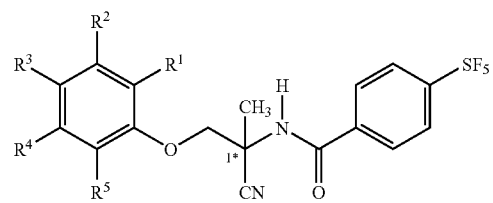

Certain compounds of formula (I) may exist as geometric isomers. The present invention encompasses such compounds in the cis (Z-) or trans (E-) configuration, as well as mixtures of these geometric isomers.

Certain compounds of formula (I) may exist in more than one tautomeric form. The present invention encompasses all such tautomers, as well as mixtures thereof.

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$ and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Certain compounds of formula (I) which have a basic functional group are able to form addition salts with acids. Certain compounds of formula (I) which have an acidic functional group are able to form salts with suitable bases. Such salts are included within the scope of the present invention to the extent that they are acceptable for veterinary or pharmaceutical use.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent.

The compounds of formula (I) and their salts may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of formula (I) and their salts may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Pharmaceutically acceptable solvates in accordance with the invention include those wherein the solvent of crystallization may be isotopically substituted, e.g. $D_2O$, $d_6$-acetone, $d_6$-DMSO.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of formula (I) and their salts may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO⁻Na⁺, —COO⁻K⁺, or —SO₃⁻Na⁺) or non-ionic (such as —N⁻N⁺(CH₃)₃) polar head group. For more information, see *Crystals and the Polarizing Microscope* by N. H. Hartshorne and A. Stuart, 4th Edition (Edward Arnold, 1970).

Hereinafter all references to compounds of formula (I) include references to salts, solvates, multi-component complexes and liquid crystals thereof and to solvates, multi-component complexes and liquid crystals of salts thereof.

In a preferred embodiment of the compounds of formula (I), $R^1$, $R^2$, $R^3$, $R^4$ and $R^5$ are each independently selected from H, F, Cl, Br, CN and CF₃. More preferably, at least one of $R^1$, $R^2$, $R^3$, $R^4$ and $R^5$ is CN and at least two of $R^1$, $R^2$, $R^3$, $R^4$ and $R^5$ are H. More preferably still, $R^1$ and $R^4$ are H, one of $R^2$ and $R^3$ is H and the other is CN, and $R^5$ is selected from F, Cl, Br and CF₃.

In a further preferred embodiment of the compounds of formula (I), $R^1$, $R^4$ and $R^5$ are each independently selected from H, halo and CF₃ and one of $R^2$ and $R^3$ is CN and the other is selected from H and CN.

In a further preferred embodiment of the compounds of formula (I), $R^1$ and $R^4$ are each H, and $R^5$ is selected from Cl, Br and CF₃.

In a further preferred embodiment of the compounds of formula (I), $R^1$, $R^2$, $R^3$, $R^4$ and $R^5$ are each independently selected from H, CN and CF₃.

In a further preferred embodiment of the compounds of formula (I), $R^1$, $R^2$ and $R^4$ are each H.

In a further preferred embodiment of the compounds of formula (I), $R^3$ is CN.

In a further preferred embodiment of the compounds of formula (I), $R^5$ is CF₃.

Particularly preferred compounds according to formula (I) include:

N-{1-cyano-2-[5-cyano-2-(trifluoromethyl)phenoxy]-1-methylethyl}-4-pentafluorothiobenzamide,
N-{(1R)-1-cyano-2-[5-cyano-2-(trifluoromethyl)phenoxy]-1-methylethyl}-4-pentafluorothiobenzamide,
N-{(1S)-1-cyano-2-[5-cyano-2-(trifluoromethyl)phenoxy]-1-methylethyl}-4-pentafluorothiobenzamide,
N-[2-(2-chloro-5-cyanophenoxy)-1-cyano-1-methylethyl]-4-pentafluorothiobenzamide,
N-[2-(2-chloro-5-cyanophenoxy)-(1R)-1-cyano-1-methylethyl]-4-pentafluorothiobenzamide,
N-[2-(2-chloro-5-cyanophenoxy)-(1S)-1-cyano-1-methylethyl]-4-pentafluorothiobenzamide,
N-{1-cyano-2-[4-cyano-2-(trifluoromethyl)phenoxy]-1-methylethyl}-4-pentafluorothiobenzamide,
N-{(1R)1-cyano-2-[4-cyano-2-(trifluoromethyl)phenoxy]-1-methylethyl}-4-pentafluorothiobenzamide,
N-{(1S)1-cyano-2-[4-cyano-2-(trifluoromethyl)phenoxy]-1-methylethyl}-4-pentafluorothiobenzamide,
N-{2-[2-chloro-5-cyano-3-(trifluoromethyl)phenoxy]-1-cyano-1-methylethyl}-4-pentafluorothiobenzamide,
N-{2-[2-chloro-5-cyano-3-(trifluoromethyl)phenoxy]-(1R)-1-cyano-1-methylethyl}-4-pentafluorothiobenzamide,
N-{2-[2-chloro-5-cyano-3-(trifluoromethyl)phenoxy]-(1S)-1-cyano-1-methylethyl}-4-pentafluorothiobenzamide,
N-[2-(2-chloro-4,5-dicyanophenoxy)-1-cyano-1-methylethyl]-4-pentafluorothiobenzamide,
N-[2-(2-chloro-4,5-dicyanophenoxy)-(1R)-1-cyano-1-methylethyl]-4-pentafluorothiobenzamide,
N-[2-(2-chloro-4,5-dicyanophenoxy)-(1S)-1-cyano-1-methylethyl]-4-pentafluorothiobenzamide,
N-(1-cyano-2-[4-cyano-2-(trifluoromethyl)phenoxy]-1-methylethyl}-4-pentafluorothiobenzamide,
N-{(1R)-1-cyano-2-[4-cyano-2-(trifluoromethyl)phenoxy]-1-methylethyl}-4-pentafluorothiobenzamide, and
N-{(1S)-1-cyano-2-[4-cyano-2-(trifluoromethyl)phenoxy]-1-methylethyl}-4-pentafluorothiobenzamide, and pharmaceutically acceptable salts thereof.

A further preferred compound according to formula (I) is:

N-{(1S)-1-cyano-2-[4-cyano-2-(trifluoromethyl)phenoxy]-1-methylethyl}-4-pentafluorothiobenzamide and pharmaceutically acceptable salts thereof.

In a further aspect, the present invention provides processes for the preparation of a compound of formula (I), or a pharmaceutically, veterinarily or agriculturally acceptable salt thereof, or a pharmaceutically, veterinarily or agriculturally acceptable solvate (including hydrate) of either entity, as illustrated below.

It will be apparent to those skilled in the art that sensitive functional groups may need to be protected and deprotected during synthesis of a compound of the invention. This may be achieved by conventional methods, for example as described in "Protective Groups in Organic Synthesis" by TW Greene and PGM Wuts, John Wiley & Sons Inc (1999), and references therein.

The following processes are illustrative of the general synthetic procedures which may be adopted in order to obtain the compounds of the invention.

When one or more of $R^1$, $R^2$, $R^3$, $R^4$, and $R^5$ contain reactive functional groups then additional protection may be provided according to standard procedures during the synthesis of compounds of formula (I). In the processes described below, for all synthetic precursors used in the synthesis of compounds of formula (I), the definitions of $R^1$, $R^2$, $R^3$, $R^4$, and $R^5$ wherein $R^1$, $R^2$, $R^3$, $R^4$, and $R^5$ are as defined for formula (I), are intended to optionally include suitably protected variants, $P^1$, $P^2$ $P^3$, $P^4$ and $P^5$. Such suitable protecting groups for these functionalities are described in the references listed herein and the use of these protecting groups where needed is specifically intended to fall within the scope of the processes described in the present invention for producing compounds of formula (I) and its precursors. When suitable protecting groups are used, then these will need to be removed to yield compounds of formula (I). Deprotection can be effected according to standard procedures including those described in the references listed herein.

1 Synthesis of Compounds of Formula (I)

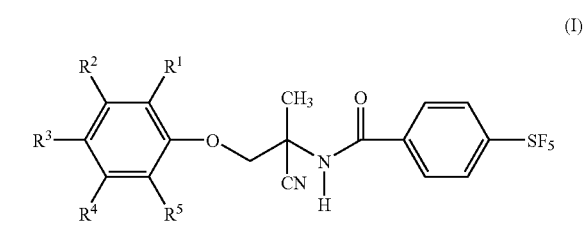

(I)

1.1 Amide Bond Formation

Compounds of formula (I) wherein $R^1$, $R^2$, $R^3$, $R^4$, and $R^5$, are as defined for formula (I) may be synthesised by the coupling of amino-nitriles of formula (II), wherein $R^1$, $R^2$, $R^3$, $R^4$, and $R^5$ are as defined for formula (I) with the acid of formula (III), or suitably activated acid derivatives such as acyl halides, esters or anhydrides.

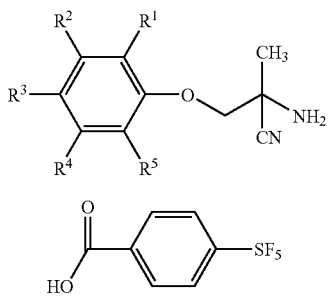

Those skilled in the art will recognise that many standard literature reaction conditions may be used to effect such amide formation; some of these are reviewed in "Amide bond formation and peptide coupling", C. A. G. N. Montalbetti and V. Falque, Tetrahedron, 2005, 61, 10827-10852.

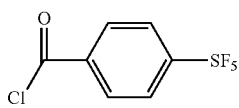

For example, amino-nitriles of formula (II) may be reacted with the acid chloride of formula (IV) in a dipolar aprotic solvent, such as tetrahydrofuran, in the presence of a base, such as diisopropylethylamine, at reduced temperature, typically 0° C. for 2 to 24 hours. Alternatively, the acid of formula (III) may be reacted with amino-nitriles of formula (II), in a polar solvent, such as N,N-dimethylformamide in the presence of O-(ethoxycarbonyl)cyanomethyleneamino)-N,N,N', N'-tetramethyluronium tetrafluoroborate, and in the presence of a base, such as diisopropylethylamine, at reduced temperature, typically 0° C. for 2 to 24 hours, in an inert atmosphere.

1.2 Nucleophilic Displacement of Aryl Halides

Compounds of formula (I) wherein $R^1$, $R^2$, $R^3$, $R^4$, and $R^5$ are as defined for formula (I), may also be synthesised by the reaction of the alcohol of formula (V) with aryl halides of formula (VI) wherein $R^1$, $R^2$, $R^3$, $R^4$ and $R^5$ are as defined for formula (I) and Hal=fluoro or chloro, preferably fluoro.

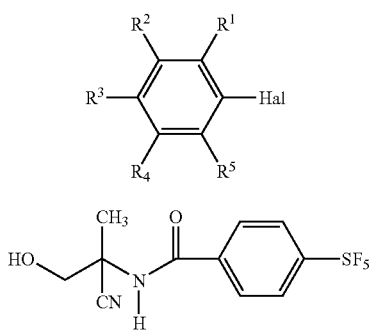

For example, potassium tert-butoxide is added at reduced temperature, typically 0° C., to a solution of the compound of formula (V) and compounds of formula (VI) in a dipolar aprotic solvent, such as tetrahydrofuran, followed by reaction at room temperature for an extended period of time, typically 16-24 hours, optionally under nitrogen. Alternatively, potassium tert-butoxide is added at room temperature to a solution of compounds of formula (V) and compounds of formula (VI) in a dipolar aprotic solvent, such as tetrahydrofuran, followed by reaction at temperatures ranging from 55° C.-75° C., typically 65° C. for an extended period of time, typically 16-24 hours, optionally under nitrogen. Other bases, such as sodium hydride may be used in suitable solvents, typically N,N-dimethylformamide, optionally in an inert atmosphere. Alternatively, potassium tert-butoxide in tetrahydrofuran is added to a solution of the compound of formula (V) and compounds of formula (VI) in dimethyl sulphoxide followed by reaction at room temperature for an extended period of time, typically 16-24 hours, optionally under nitrogen. When using some aryl fluorides of formula (VI), wherein Hal=fluorine, anhydrous dimethyl sulphoxide is required for this reaction.

The individual enantiomers of the alcohol of formula (V) may be obtained from the racemate by chiral hplc using standard literature chromatographic conditions. For example using methanol/ethanol/hexane mixtures as eluants on a 500 mm×50 mm ID Chiralcel AD-H 5 μm with a flow rate of 5 ml/min. These enantiomers of formula (V) may also be used in the nucleophilic displacement reaction to yield individual enantiomers of the compounds of formula (I).

For this reaction, when using compounds of formula (VI), wherein Hal=fluorine and one or more of $R^1$, $R^2$, $R^3$, $R^4$ or $R^5$ is also fluorine, then each individual fluorine atom is susceptible to substitution yielding mixtures of regioisomers.

1.3 Synthesis of Amino-nitrites of Formula (II)

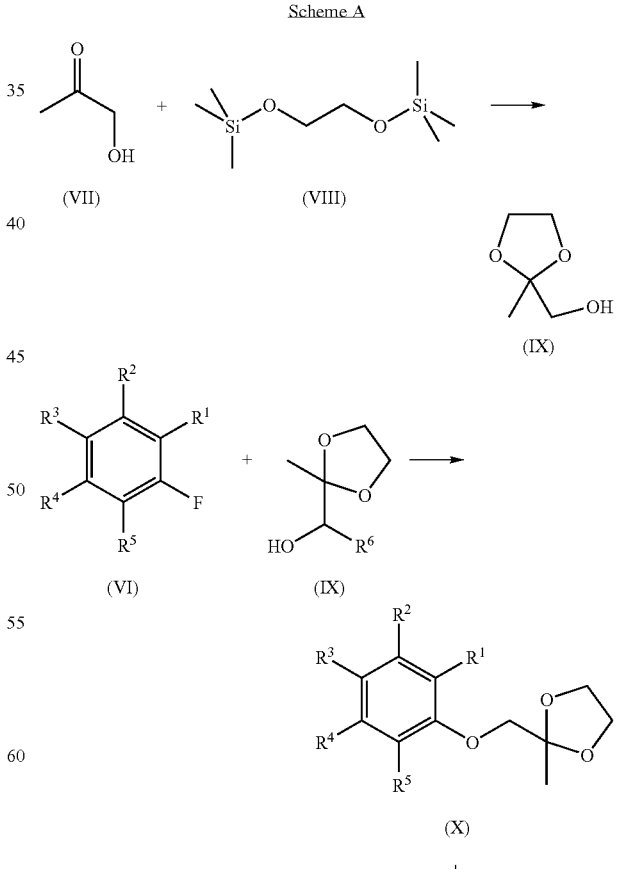

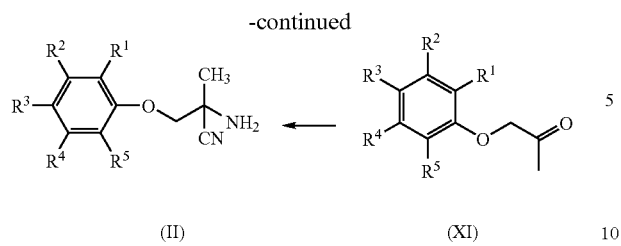

Compounds of formula (II) wherein R¹, R², R³, R⁴, and R⁵ are as defined for formula (I) may be synthesised as shown in Scheme A.

Hydroxyacetone of formula (VII) may be protected as the ethylene ketal of formula (IX) by reaction with 1,2-bis(trimethylsilyloxy)ethane, the compound of formula (VIII), and trimethylsilyl trifluoromethanesulphonate in an anhydrous dipolar aprotic solvent, such as tetrahydrofuran at room temperature for 10-30 hours, typically 18 hours.

Compounds of formula (X), wherein R¹, R², R³, R⁴, and R⁵ are as defined for formula (I), may be synthesised by the reaction of the ethylene ketal of formula (IX) with the aryl fluorides of formula (VI). For example, potassium tert-butoxide is added at reduced temperature, typically 0° C., to a solution of compounds of formula (IX) and compounds of formula (VI) in a dipolar aprotic solvent, such as tetrahydrofuran, followed by reaction at room temperature for an extended period of time, typically 16-24 hours, optionally under nitrogen. The ketals of formula (X) may be deprotected to afford the phenoxyketones of formula (XI) by refluxing in acetone in the presence of an acid catalyst, such as 2M hydrochloric acid, for periods ranging from 15-30 hours, typically 20 hours. The amino-nitriles of formula (II) may be prepared from the ketones of formula (XI) using standard literature Strecker synthesis conditions. For example, the ketones of formula (XI) may be reacted with ammonium chloride in methanolic ammonia at room temperature for 15-45 minutes followed by the addition of sodium cyanide and continuing the reaction at room temperature for 15-70 hours.

Amino-nitriles of formula (II) wherein R¹, R², R³, R⁴, and R⁶ are as defined for formula (I) have a single stereocentre alpha to the nitrile, provided R¹, R², R³, R⁴, and R⁵ lack stereocentres. Such compounds may be prepared stereochemically pure using a variety of literature asymmetric Strecker syntheses. Some of these procedures are described in Org. Letters, 2000, 2, 6, 867-870; Tetrahedron—Asymmetry 2001, 12, 1147-1150; J. Amer. Chem. Soc. 2003, 125, 5634-5635; J. Amer. Chem. Soc., 1998, 120, 5315-5316; Tetrahedron Letters, 1996, 37, 33, 5839-5840; and Org. Letters, 2004, 5, 26, 5027-5029.

1.4 Acid Chloride of Formula (IV)

4-Pentafluorothiobenzoyl chloride may be prepared according to Scheme B.

Scheme B

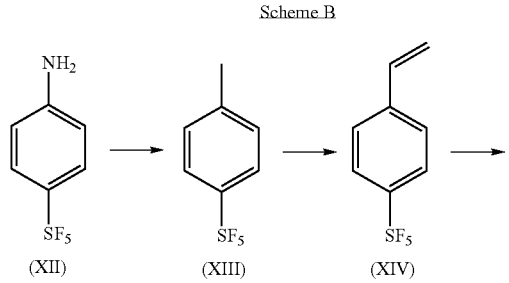

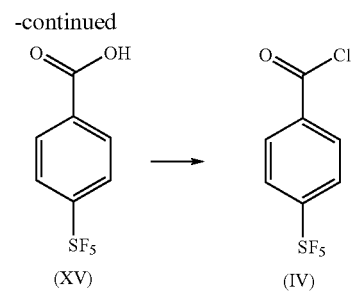

1-Iodo-4-(pentafluorothio)benzene, the compound of formula (XIII), may be prepared by the reaction of the diazonium salt formed by the reaction of 4-(pentafluorothio)aniline with sodium nitrite in aqueous hydrochloric acid, with potassium iodide. The diazonium salt is preferably formed at 0° C.; the subsequent iodination may take place at room temperature over a period of 18-60 hours. The alkene of formula (XIV) may be prepared by reaction of the iodo compound of formula (XIII) with tributyl(vinyltin using a tetrakis(triphenylphosphine)palladium(0) catalyst in a polar solvent, such as N,N-dimethyl formamide at 10000, under nitrogen, for 1-5 hours, typically 1.5 hours. The acid of formula (XV) may be prepared by oxidation of the alkene, of formula (XIV) using, for example, sodium periodate in an acetonitrile/carbon tetrachloride/water solvent mix in the presence of a ruthenium (III) chloride hydrate catalyst, under an inert atmosphere, at room temperature for 1-20 hours. The acid chloride of formula (IV) may be prepared from the acid of formula (XV) using literature procedures well know to those skilled in the art. Typically heating with excess thionyl chloride at 65° C. for 2-4 hours.

The acid of formula (XV) may be prepared directly from the compound of formula (XIII) by reaction of carbon dioxide with an organometallic species generated from (XIII); for example using isopropyl magnesium chloride in an anhydrous aprotic solvent such as tetrahydrofuran.

Compounds of formula (XV) and (IV) may also be obtained commercially.

1.5 Synthesis of the Amido-alcohol of Formula (V)

Scheme C

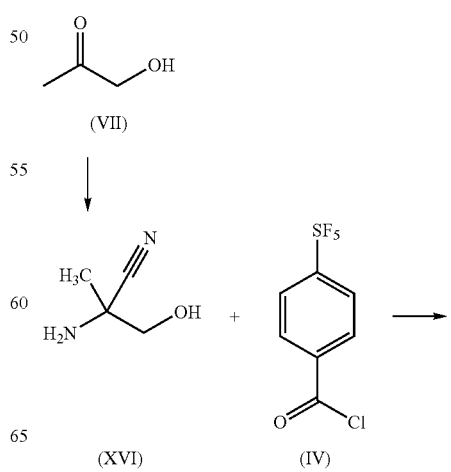

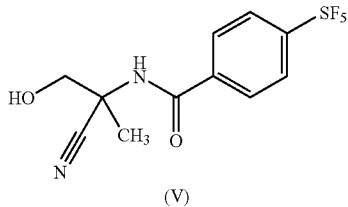

(V)

The amido-alcohol of formula (V) may be prepared as shown in Scheme C. The amino-nitrile of formula (XVI) may be prepared from hydroxylacetone of formula (VII) using standard literature Strecker synthesis conditions. For example, the hydroxyacetone may be reacted with ammonium chloride in methanolic ammonia at room temperature for 15-45 minutes followed by the addition of sodium cyanide and continuing the reaction at room temperature for 15-25 hours. The amide of formula (V) may be prepared by the reaction of the acid chloride of formula (IV), with the amino-nitrile of formula (XVI). For example, the amino-nitrile of formula (XVI) may be reacted with acid chlorides of formula (IV), wherein $R^7$, $R^8$, $R^9$, $R^{10}$ and $R^{11}$ in a dipolar aprotic solvent, such as tetrahydrofuran, in the presence of a base, such as diisopropylethylamine, at reduced temperature, typically 0° C. for 2 to 24 hours.

1.6 Aryl Halides of Formula (VI)

Most of the aryl halides of formula (VI) are commercially available or may be prepared by standard literature procedures well known to those skilled in the art. The following examples illustrate some successful synthetic conversions and does not represent an all inclusive list.

4-cyano-2-fluorobenzamide may be prepared by the ammonolysis of 4-cyano-2-fluorobenzoic acid using aqueous ammonium hydroxide (35%) in a suitable solvent, such as acetonitrile, in the presence of 1,1'-dicarbonyldiimidazole. 2-Fluoroterephthalonitrile may be prepared from 4-cyano-2-fluorobenzamide by reaction with palladium (II) chloride in a suitable solvent, such as acetonitrile, at temperatures ranging from 30°-60° C., typically 50° C. for 15-30 hours, typically 24 hours. 4-Fluoroisophthalonitrile may be prepared from 2-fluoro-5-formylbenzonitrile by reaction with hydroxylamine-O-sulphonic acid in aqueous solution at 50° C. for several hours, normally 5 hours.

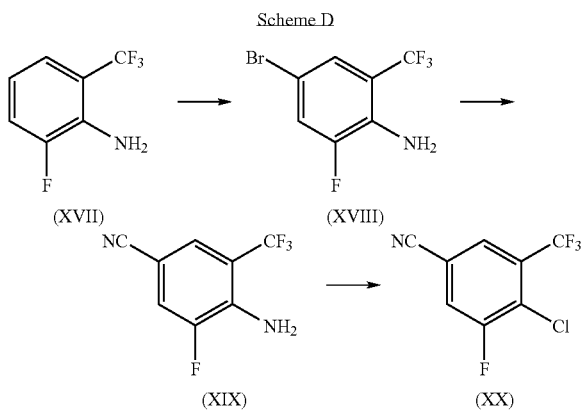

Scheme D

Scheme D shows the preparation of 4-chloro-3-fluoro-5-(trifluoromethyl)benzonitrile, compound (XX). Compound (XVIII) may be prepared by bromination of 2-amino-3-fluorobenzotrifluoride using N-bromosuccinimide in a suitable solvent, such as acetonitrile, in the presence of iron (III) chloride. The nitrite (XIX) may be prepared from compound (XVIII) by reaction with sodium cyanide in a suitable solvent, such as 1-methyl-2-pyrrolidinone, in the presence of nickel (II) bromide, by heating in a microwave oven (typical model CEM 300W) at 160° C. for several hours, normally 6 hours Compound (XIX) may be converted to compound (XX) by standard Sandmeyer conditions using tert-butyl nitrite and copper (1) chloride Methyl 5-cyano-2-fluorobenzoate may be prepared from 3-bromo-4-fluorobenzonitrile by heating in methanol at 60° C., under a carbon monoxide atmosphere in the presence of a base, such as triethylamine, and a suitable catalyst, typically [1,1'-bis(diphenylphosphino)ferrocene]dichloropalladium (II).

2 Functional Group Interconversions.

The substituents, $R^1$, $R^2$, $R^3$, $R^4$ and $R^5$, wherein as defined for compounds of formula (I), in compounds of formula (I) or compounds of formula (V), may be converted, where chemically feasible, to other substituents, $R^1$, $R^2$, $R^3$, $R^4$ and $R^5$ as defined for compounds of formula (I).

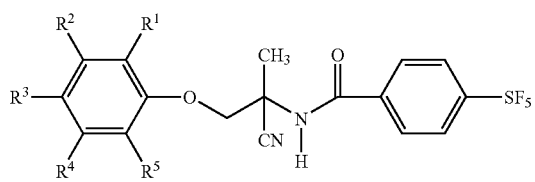

(XXI)

Compounds of formula (I), wherein one of $R^1$, $R^2$, $R^3$, $R^4$ and $R^5$=—C(O)NH$_2$ may be prepared from the corresponding compounds of formula (XXI), wherein one of $R^1$, $R^2$, $R^3$, $R^4$ and $R^5$=—C(O)OH using standard literature methods. Those skilled in the art will recognise that many standard literature reaction conditions may be used to effect such amide formation; some of these are reviewed in "Amide bond formation and peptide coupling" C. A. G. N. Montalbetti and V. Falque, Tetrahedron, 2005, 61, 10827-10852.

Acids of formula (XXI) wherein one of $R^1$, $R^2$, $R^3$, $R^4$, $R^5$=C(O)OH and the others of $R^1$, $R^2$, $R^3$, $R^4$, and $R^5$ are as defined for compounds of formula (I) may be prepared from the corresponding alkyl esters by reaction with lithium hydroxide monohydrate in tetrahydrofuran:water (1:1) at room temperature overnight. Acids may be converted to methyl esters by reaction with diazomethane or (trimethylsilyl)diazomethane The alkyl esters of formula (XXI), wherein one of $R^1$, $R^2$, $R^3$, $R^4$ and $R^5$=—C(O)O-alkyl may be obtained from the corresponding bromo compounds by the Pd-catalysed carbonylation using carbon monoxide in the presence of alcohols in a solvent such as N,N-dimethyl formamide. These esters may be directly converted to amides using literature procedures well known to those skilled in the art.

These bromo compounds may also undergo a variety of organometallic coupling reactions. For these reactions, other sensitive functional groups elsewhere in the molecule may require appropriate protection. For example, lithiation using butyl lithium in aprotic solvents, such as tetrahydrofuran, in an inert atmosphere, gives intermediate aryl lithium species which may be reacted with chloroformate esters to give compounds of formula (I) or compounds of formula (V), wherein one of $R^1$, $R^2$, $R^3$, $R^4$ and $R^5$=—COOMe.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps.

The skilled person will appreciate that the compounds of the invention could be made by methods other than those herein described, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

It is to be understood that the synthetic transformation methods mentioned herein are exemplary only and they may be carried out in various different sequences in order that the desired compounds can be efficiently assembled. The skilled chemist will exercise his judgement and skill as to the most efficient sequence of reactions for synthesis of a given target compound.

The compounds of formula (I) have antiparasitic activity and so are useful in the control of parasitic infestations in host animals.

The parasite may be an endoparasite, such as a helminth, or an ectoparasite, such as an arthropod.

Examples of helminths include parasites of the phylum Platyhelminthes (such as cestodes and trematodes; e.g. *Fasciola* spp.; *Fascioloides* spp.; *Paramphistomum* spp.; *Dicrocoelium* spp.; *Eurytrema* spp., *Ophisthorchis* spp.; *Fasciolopsis* spp.; *Echinostoma* spp.; *Paragonimus* spp.) and the phylum Nematoda (such as filarial, intestinal and tissue nematodes; e.g. *Haemonchus* spp.; *Ostertagia* spp.; *Cooperia* spp.; *Oesphagastomum* spp.; *Nematodirus* spp.; *Dictyocaulus* spp.; *Trichuris* spp.; *Toxocara* spp.; *Toxascaris* spp.; *Trichinella* spp.; *Dirofilaria* spp.; *Ancyclostoma* spp.; *Necator* spp.; *Strongyloides* spp.; *Capillaria* spp.; *Ascaris* spp.; *Enterobius* spp.; and *Trichostrongylus* spp.).

Examples of arthropods include Acarina, including ticks (e.g. *Ixodes* spp., *Boophilus* spp. e.g. *Boophilus microplus, Amblyomma* spp., *Hyalomma* spp., *Rhipicephalus* spp. e.g. *Rhipicephalus appendiculatus, Haemaphysatis* spp., *Dermacentor* spp., *Ornithodorus* spp. (e.g. *Ornithodorus moubata*)), mites (e.g. *Damatinia* spp., *Dermanyssus gallinae, Sarcoptes* spp. e.g. *Sarcoptes scabiei, Psoroptes* spp., *Chorioptes* spp., *Demodex* spp., *Eutrombicula* spp.); Diptera (e.g. *Aedes* spp., *Anopheles* spp., *Muscidae* spp. e.g. *Stomoxys caicitrans* and *Haematobia irritans, Hypoderma* spp., *Gastrophilus* spp., *Simulium* spp.) Hemiptera (e.g. *Triatoma* spp.); Phthiraptera (e.g. *Damalinia* spp., *Linognathus* spp.); Siphonaptera(e.g. *Ctenocephalides* spp.); Dictyoptera (e.g. *Periplaneta* spp., *Blatella* spp.) and Hymenoptera (e.g. *Monomorium pharaonis*).

The compounds of formula (I) are particularly useful for the control of helminth infestations.

The host animal may be a mammal or a non-mammal, such as a bird or a fish. Where the host animal is a mammal, it may be a human or non-human mammal. Non-human mammals include livestock animals and companion animals, such as cattle, sheep, goats, equines, swine, dogs and cats.

The compounds of formula (I) may be administered by any suitable route. Examples of suitable routes of administration include oral, topical and parenteral administration. The choice of the route will depend on the species of the host animal and the nature of the parasitic infestation. For example, oral administration might be preferred in the case of a human or companion animal host, or for the treatment of endoparasites, while topical administration might be more convenient for treating large numbers of livestock animals such as a herd of cattle.

The compounds of formula (I) may be administered alone or in a formulation appropriate to the specific use envisaged. Generally, they will be administered as a formulation in association with one or more pharmaceutically acceptable excipients.

The term "excipient" is used herein to describe any ingredient other than the active components. The choice of excipient will to a large extent depend on factors such as the particular mode of administration, the effect of the excipient on solubility and stability, and the nature of the dosage form.

The compounds of formula (I) may be administered as crystalline or amorphous products, for example, spray-dried dispersions or as produced by melt-extrusion or nano-milling. They may be obtained, for example, as solid plugs, powders, or films (for example, rapid dissolving or mucoadhesive films) by methods such as precipitation, crystallization, freeze drying, or spray drying, or evaporative drying. Microwave or radio frequency drying may be used for this purpose.

The methods by which the compounds of formula (I) may be administered include oral administration by capsule, bolus, tablet, powders, lozenges, chews, multi and nanoparticulates, gels, solid solution, films, sprays, or liquid formulation. Liquid forms include suspensions, solutions, syrups, drenches and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. Oral drenches are commonly prepared by dissolving or suspending the active ingredient in a suitable medium.

Thus compositions useful for oral administration may be prepared by mixing the active ingredient with a suitable finely divided diluent and/or disintegrating agent and/or binder, and/or lubricant etc. Other possible ingredients include antioxidants, colourants, flavouring agents, preservatives and taste-masking agents.

For oral dosage forms, depending on dose, the drug may make up from 1 wt % to 80 wt % of the dosage form, more typically from 5 wt % to 60 wt % of the dosage form. Examples of suitable disintegrants for use herein include sodium starch glycolate, sodium carboxymethyl cellulose, calcium carboxymethyl cellulose, croscarmellose sodium, crospovidone, polyvinylpyrrolidone, methyl cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation.

Examples of suitable binders for use herein include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Examples of diluents include lactose (monohydrate, spray-dried monohydrate, anhydrous and the like), mannitol, xylitol, dextrose, sucrose, sorbitol, microcrystalline cellulose, starch and dibasic calcium phosphate dihydrate.

Oral formulations may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Lubricants include magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The compounds of formula (I) may be administered topically to the skin, that is dermally or transdermally. The compounds may also be administered via the mucosa or mucous membranes. Typical formulations for this purpose include pour-on, spot-on, dip, spray, mousse, shampoo, powder formulation, gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm Sci, 88 (10), 955-958 by Finnin and Morgan (October 1999). Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal.

Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient. These formulations may be self-preserving, self-sterilising or may be non-sterile to which preservatives may be optionally added.

Equally suitably the compounds of formula (I) can be administered parenterally, or by injection directly into the blood stream, muscle or into an internal organ. Suitable routes for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as powdered a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The solubility of compounds of formula (I) used in the preparation of parenteral solutions may be increased by the use of appropriate formulation techniques, such as the incorporation of solubility-enhancing agents.

Such formulations are prepared in a conventional manner in accordance with standard medicinal or veterinary practice.

These formulations will vary with regard to the weight of active compound contained therein, depending on the species of host animal to be treated, the severity and type of infection and the body weight of the host. For parenteral, topical and oral administration, typical dose ranges of the active ingredient are 0.01 to 100 mg per kg of body weight of the animal. Preferably the range is 0.1 to 10 mg per kg.

Formulations may be immediate release or be designed to have a controlled or modified release profile. Modified release formulations include those formulations which have a delayed-, sustained-, pulsed-, targeted, or programmed release. Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298. Alternatively, compounds of the invention may be formulated as a solid, semi-solid, or thixotropic liquid for administration as an implanted depot providing modified release of the active compound. Examples of such formulations include drug-coated stents and PGLA microspheres.

As an alternative the compounds of formula (I) may be administered to a non-human animal with the feedstuff and for this purpose a concentrated feed additive or premix may be prepared for mixing with the normal animal feed.

The compounds of formula (I) may advantageously be used in combination with one or more further therapeutic agents, including, but not limited to, further antiparasitic agents.

Examples of antiparasitic agents that may be used in combination with the compounds of formula (I) include anthelmintic agents, fasciolicides and ectoparasiticides.

In one embodiment of the invention, the compounds of formula (I) are used in combination with a second anthelmintic agent. Such a combination may reduce the likelihood of resistance developing. Suitable further anthelmintic agents include:

the macrocyclic lactone class of compounds (such as ivermectin, avermectin, abamectin, emamectin, eprinomectin, doramectin, selamectin, moxidectin, nemadectin, milbemycin and milbemycin derivatives such as those described in EP-357460, EP-444964 and EP-594291, and semisynthetic and biosynthetic avermectin/milbemycin derivatives such as those described in U.S. Pat. No. 5,015,630, WO-9415944 and WO-9522552);

benzimidazoles (such as albendazole, cambendazole, fenbendazole, flubendazole, mebendazole, oxfendazole, oxibendazole and parbendazole);

imidazothiazoles and tetrahydropyrimidines (such as tetramisole, levamisole, pyrantel pamoate, oxantel or morantel);

derivatives and analogues of the paraherquamide/marcfortine class of anthelmintic agents, particularly 2-desoxoparaherquamide;

nitroscanate;

antiparasitic oxazolines (such as those disclosed in U.S. Pat. No. 5,478,855, U.S. Pat. No. 4,639,771 and DE-19520936);

derivatives and analogues of the general class of dioxomorpholine antiparasitic agents as described in WO-9615121; and cyclic depsipeptides (such as those described in WO-9611945, WO-9319053, WO-9325543, EP-626375, EP-382173, WO-9419334, EP-382173, and EP-503538, and particularly emodepside).

In a preferred embodiment, the compounds of formula (I) are used in combination with a macrocyclic lactone anthelmintic agent selected from ivermectin, avermectin, abamectin, emamectin, eprinomectin, doramectin, selamectin, moxidectin, nemadectin and milbemycin oxime.

In another preferred embodiment, the compounds of formula (I) are used in combination with a benzimidazole anthelmintic agent selected from albendazole, cambendazole, fenbendazole, flubendazole, mebendazole, oxfendazole, oxibendazole and parbendazole.

In another preferred embodiment, the compounds of formula (I) are used in combination with an anthelmintic agent selected from tetramisole, levamisole, pyrantel pamoate, oxantel and morantel.

In another preferred embodiment, the compounds of formula (I) are used in combination with derivatives and analogues of the paraherquamide/marcfortine class of anthelmintic agents, particularly 2-desoxoparaherquamide.

In another embodiment of the invention, the compounds of formula (I) are used in combination with a flukicide, for example a fasciolicide. Suitable agents include closantel, triciabendazole, clorsulon, rafoxanide, niclosamide, praziquantel and epsiprantel.

In another embodiment of the invention, the compounds of formula (I) are used in combination with an ectoparasiticidal agent. Suitable agents include:
  aryl pyrazoles (such as fipronil, pyriprole, pyrafluprole and the like);
  pyrethroids;
  organophosphates;
  insect growth regulators (such as lufenuron and the like);
  spiroketoenol insecticides (such as spiromesifen and the like);
  ecdysone agonists (such as tebufenozide and the like);
  spinosyns (such as spinosad, spinetoram and the like, especially spinetoram);
  neonicotinoids (such as imidacloprid, dinotefuran and the like) and
  other insecticides (such as metaflumizone, flubendiamide, chlorantraniliprole, indoxacarb, pyridalyl, pyrimidifen and pyrifluquinazon, especially metaflumizone, indoxacarb and flubendiamide).

In another preferred embodiment, the compounds of formula (I) are used in combination with an ectoparasiticidal agent selected from fipronil, pyriprole, pyrafluprole lufenuron, spiromesifen, tebufenozide, tebufenozide, spinosad, spinetoram, imidacloprid, dinotefuran, metaflumizone, flubendiamide, chlorantraniliprole, indoxacarb, pyridalyl, pyrimidifen and pyrifluquinazon.

When the compounds of formula (I) are used to treat a parasitic infestation in a livestock animal then they may be used in combination with any of the agents commonly known in the art to be useful as feed additives for such livestock animals, and which are described in such manuals as "2006 Feed Additive Companion" and "Handbook of Feed Additives 2006". Suitable agents include:
  polyether ionophores (such as lasalocid, monensin, salinomycin, narasin and laidlomycin);
  antibiotics (such as the tetracyclines, bacitracin, tylosin, tiamulin, lincomycin, virginiamycin, quinolone antibacterials and carbadox);
  steroid derivatives (such as melengesterol acetate);
  agents for the prevention or treatment of sub-acute rumen acidosis (such as sodium bicarbonate, acarbose and other amylase or glucosidase inhibitors);
  carcass quality/anabolic agents (such as beta adrenergic ligands, including ractopamine, salbutamol and almeterol); and
  other supplements (such as enzymes, minerals and vitamins).

The two components may be administered simultaneously, sequentially or separately. Where the two components are administered sequentially or separately then they may both be given by the same route, or they may be administered by different routes.

As used herein, simultaneous administration means the administration of both components to the host animal in a single action, which requires the two components to be incorporated into a single dosage unit, such as a single tablet or a single pour-on solution.

Sequential administration means the administration of each component is a separate action, but the two actions are linked. For example, administering a tablet comprising one component and a second tablet comprising the second component is considered to be sequential administration, even if the two tablets are given to the host animal at the same time.

Separate administration refers to the administration of each component independently of the other.

For convenience, simultaneous administration may be preferable.

The two components may be presented in kit form. Such a kit comprises two or more separate pharmaceutical compositions, at least one of which contains a compound of formula (I) and one contains a further antiparasitic agent, and means for separately retaining said compositions, such as a container, divided bottle, or divided foil packet. An example of such a kit is the familiar blister pack used for the packaging of tablets, capsules and the like.

The kit is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

EXAMPLES

The following Examples illustrate the preparation of compounds of the formula (I).

In the following experimental details, nuclear magnetic resonance (N.m.r.) spectral data were obtained using Varian Inova 300, Varian Inova 400, Varian Mercury 400, Varian Unityplus 400, Bruker AC 300 MHz, Bruker AM 250 MHz or Varian T60 MHz spectrometers, the observed chemical shifts being consistent with the proposed structures. N.m.r. chemical shifts are quoted in p.p.m downfield from tetramethylsilane. In the following Examples, where an Example is indicated as being a mixture of diastereoisomers, then the n.m.r. integrals shown refer to the relative ratio of integrals for the quoted chemical shift. Mass spectral data were obtained on a Finnigan ThermoQuest Aqa, a Waters micromass ZQ, or a Hewlett Packard GCMS System Model 5971 spectrometer. The calculated and observed ions quoted refer to the isotopic composition of lowest mass. HPLC means high performance liquid chromatography. Room temperature means 20 to 25° C. Where an Example is indicated as being a mixture of regioisomers, the biological data refers to a mixture of compounds with the quoted ratios.

When the source of a simple precursor is unspecified these compounds may be obtained from commercial suppliers or according to literature procedures. The following is a list of commercial suppliers for such compounds:

Sigma-Aldrich, P O Box 14508, St. Louis, Mo., 63178, USA

Fluorochem Ltd., Wesley Street, Old Glossop, Derbyshire, SK13 7RY, UK

Alfa Aesar, 26 Parkridge Road, Ward Hill, Mass., 01835, USA

Apollo Scientific Ltd., Whitefield Rd., Bredbury, Stockport, Cheshire, SK6 2QR, UK Fluka Chemie GmbH, Industriestrasse 25, P.O. Box 260, CH-9471 Buchs, Switzerland ChemPur GmbH, Rueppurrer Str. 92, Karlsruhe, D-76137, Germany Biological Assay The *Haemonchus contortus* L3 (HcL3) test is used to measure the biological activities of the compounds claimed. The assay involves in vitro testing against *H. contortus* conducted according to the following general procedure.

HcL3 larvae were collected from infected sheep and, after cleaning, stored in water at 12° C. for up to one month. Viable infective larvae were exsheathed using 10% hypochlorite in Glucose Tyrodes balanced salt solution containing antibiotics and resuspended in basal medium (20 g/l bacto-tryptone, 5 g/l yeast extract, 57 g/l glucose, 0.8 g/l di-Potassium hydrogen orthophosphate, 0.8 g/l potassium dihydrogen orthophosphate and 2 μM Hepes with antibiotics). 95 μl worm suspension was added to each well of a 96 well plate.

Test compounds were dissolved in dimethylsulfoxide to give a working stock solution of 20 mg/ml. The stock concentration was diluted 1:10 in Basal media to give 2.0 mg/ml (10% DMSO). 5 μl of the stock compound solution was added to the worm suspension to give a final concentration of 100 μg/ml. Plates were sealed with pressure sensitive film and incubated at 37° C. Observations were made 2 hrs, 24 hrs, 48 hrs, 72 hrs and 4 days post-treatment using an inverted microscope. Activity was recorded if a significant proportion of the worms were dead or adversely affected by the compound when compared to the control well containing 1% DMSO. Compounds were initially tested at 100 μg/ml, wherefrom relevant dose responses (100, 30, 10, 3, 1, 0.3, 0.1 μg/ml) were conducted in duplicate experiments to generate n=2. Data was recorded as minimum effective dose.

Example 1

N-{1-cyano-2-[5-cyano-2-(trifluoromethyl)phenoxy]-1-methylethyl}-4-(pentafluorothio)benzamide

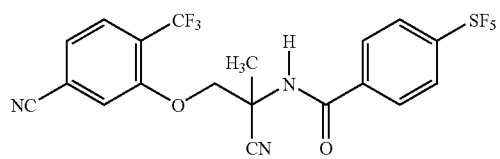

Example 1a

Racemate

To a solution of the compound of Preparation 1 (2.2 g, 8.2 mmol) and N,N-diisopropylethylamine (1.7 ml, 9.9 mmol) in tetrahydrofuran (10 ml), at 0° C., was added the compound of Preparation 2 (2.7 g, 8.2 mmol) in tetrahydrofuran (10 ml). The reaction mixture was allowed to warm to room temperature over 2 h, before addition of water (10 ml). To the mixture was added ethyl acetate (25 ml) and the two layers were separated. The organic phase was washed with aqueous potassium carbonate solution (10%, 20 ml), saturated aqueous ammonium chloride solution (20 ml) and brine, dried (MgSO$_4$) and concentrated in vacuo. The residue was triturated with tert-butyl methyl ether and the resulting precipitate was collected by filtration and dried in vacuo to give the compound of Example 1a (2.0 g).

Experimental MH$^+$ 500.0; expected 500.1

$^1$H-NMR (CDCl$_3$). 1.99-2.01 (3H), 4.45-4.48 (1H), 4.70-4.74 (H), 6.47-6.50 (1H), 7.28-7.30 (1H), 7.42-7.45 (1H), 7.71-7.75 (1H), 7.84-7.88 (4H) in vitro H.c. (L3) MED=3 μg/ml Alternative Synthesis To a solution of the compound of Preparation 1 (228 mg, 0.8 mmol) and Preparation 3 (210 mg, 0.8 mmol) in N,N-dimethylformamide (5 ml), at 0° C., was added O-((ethoxycarbonyl)cyanomethyleneamino)-N,N,N',N'-tetramethyluronium tetrafluoroborate (TOTU, 278 mg, 0.8 mmol). The reaction vessel was purged with nitrogen, before the dropwise addition of N,N-diisopropylethylamine (0.3 ml, 1.7 mmol), and the reaction mixture was allowed to warm to room temperature and stirred for 18 h. The mixture was poured into water (50 ml) and extracted with ethyl acetate (40 ml). The combined extracts were washed successively with water (20 ml), saturated aqueous sodium hydrogen carbonate solution (20 ml), water (20 ml), aqueous citric acid solution (5%, 20 ml) and brine (20 ml). The solution was dried (MgSO$_4$) and concentrated in vacuo to give the compound of Example 1a (395 mg).

Experimental (M-H$^+$)$^-$ 498.1; expected 498.1.

Example 1b

First-eluting Enantiomer and Example 1c

Second-eluting Enantiomer

The compound of Example 1a (240 mg, 0.5 mmol) was dissolved in ethanol (8 ml) and the enantiomers were separated by automated preparative liquid chromatography (Gilson system, 250×20 mm ID Chiralcel AD-H, 5 μm column, 12 ml/min) using methanol:ethanol:hexane [10:10:80] as the mobile phase. The appropriate fractions were combined and concentrated to give two enantiomerically pure products, the compound of Example 1b and the compound of Example 1c.

Example 1b: Retention time=14.50 min (250×4.6 mm Chiralcel AD-H, 5 μm column, methanol:ethanol:hexane [10:10:80], 1 ml/min)

Experimental MH$^+$ 500.1; expected 500.1

$^1$H-NMR (CDCl$_3$): 2.00-2.02 (3H), 4.41-4.44 (1H), 4.70-4.73 (1H), 6.42-6.45 (1H), 7.27-7.28 (1H), 7.40-7.42 (1H), 7.72-7.74 (1H), 7.81-7.84 (4H) in vitro H.c. (L3) MED=1 μg/ml Example 1c: Retention time=19.51 min (250×4.6 mm Chiralcel AD-H, 5 μm column, methanol:ethanol:hexane [10:10:80], 1 ml/min)

Experimental MH$^+$ 500.1; expected 500.1

$^1$H-NMR (CDCl$_3$): 1.99-2.01 (3H), 4.42-4.45 (1H), 4.70-4.73 (1H), 6.41-6.44 (1H), 7.25-7.26 (1H), 7.40-7.42 (1H), 7.72-7.74 (1H), 7.81-7.84 (4H) in vitro H.c. (L3) MED>30 μg/ml

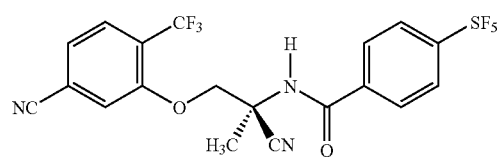

Example 1c—absolute stereochemistry as determined by single crystal X-ray analysis

Example 2

N-[2-(2-Chloro-5-cyanophenoxy)-1-cyano-1-methylethyl]-4-(pentafluorothio)benzamide

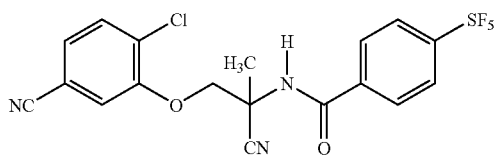

To a mixture of the compound of Preparation 9 (150 mg, 0.5 mmol) and 4-chloro-3-fluorobenzonitrile (71 mg, 0.5 mmol), under nitrogen, was added tetrahydrofuran (2 ml). The mixture was cooled to 0° C., before the dropwise addition of potassium tert-butoxide (1M in tetrahydrofuran, 0.8 ml, 0.8 mmol). The reaction mixture was allowed to warm to room temperature and stirred for 19 h. The mixture was diluted with ethyl acetate and washed with saturated aqueous ammonium chloride solution (×2), water and brine, dried (MgSO$_4$) and concentrated in vacuo. The residue was dissolved in acetonitrile (2 ml) and purified by automated preparative liquid chromatography (Gilson system, 150 mm×50 mm LUNA C18(2) 10 μm column, 120 ml/min) using an acetonitrile:water gradient [60:40 (for 15 min) to 98:2 (for 3 min) to 60:40 (for 1 min)]. The appropriate fractions were concentrated in vacuo to give the title compound (72 mg) as a racemic mixture Experimental MH$^+$ 466.0; expected 466.0

$^1$H-NMR (d$_6$-Acetone): 2.00-2.03 (3H), 4.65-4.69 (1H), 4.78-4.82 (1H), 7.40-7.43 (1H), 7.63-7.67 (2H), 8.00-8.03 (2H), 8.10-8.14 (2H), 8.56-8.60 (1H) in vitro H.c. (L3) MED=1 μg/ml

Example 3

N-{1-Cyano-2-[4-cyano-2-(trifluoromethyl)Phenoxy]-1-methylethyl}-4-(pentafluorothio)benzamide

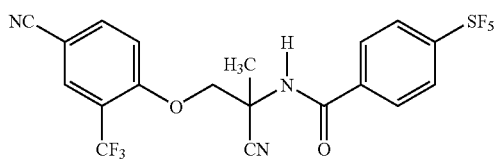

Example 3a

Racemate

To a mixture of the compound of Preparation 9 (150 mg, 0.5 mmol) and 4-fluoro-3-(trifluoromethyl)benzonitrile (86 mg, 0.5 mmol), under nitrogen, was added tetrahydrofuran (2 ml). The mixture was cooled to 0° C., before the dropwise addition of potassium tert-butoxide (1M in tetrahydrofuran, 0.8 ml, 0.8 mmol). The reaction mixture was allowed to warm to room temperature and stirred for 19 h. The mixture was diluted with ethyl acetate and washed with saturated aqueous ammonium chloride solution (×2), water and brine, dried (MgSO$_4$) and concentrated in vacuo. The residue was dissolved in methanol (2 ml) and purified by automated preparative liquid chromatography (Gilson system, 150 mm×50 mm LUNA C18(2) 10 μm column, 120 ml/min) using an acetonitrile:water gradient [55:45 (for 15 min) to 98:2 (for 3 min) to 55:45 (for 1 min)]. The appropriate fractions were concentrated in vacuo to give the compound of Example 3a (73 mg) as a racemic mixture.

Experimental MH$^+$ 499.9; expected 500.1

$^1$H-NMR (d$_6$-Acetone): 1.98-2.00 (3H), 4.78-4.80 (1H), 4.84-4.86 (1H), 7.58-7.60 (1H), 8.00-8.03 (2H), 8.08-8.12 (4H) in vitro H.c. (L3) MED=1 μg/ml

Example 3b

Single Enantiomer

To a solution of the compound of Preparation 20 (2.5 g, 7.6 mmol) and 4-fluoro-3-(trifluoromethyl)benzonitrile (2.2 g, 11.4 mmol) in tetrahydrofuran (25 ml), at −10° C., was added dropwise potassium tert-butoxide (1M in tetrahydrofuran, 15.1 ml, 15.1 mmol). The reaction mixture was stirred at −10° C. for 2 h and then quenched by addition of saturated aqueous ammonium chloride solution (80 ml). The mixture was extracted with ethyl acetate (2×40 ml) and the combined extracts were washed with water (50 ml) and brine (40 ml), dried (MgSO$_4$) and concentrated in vacuo. The residue was purified by automated flash chromatography (Biotage™, 65i silica cartridge) with gradient elution, ethyl acetate:cyclohexane [0:100 to 50:50]. The appropriate fractions were combined and concentrated and to the residue was added ethyl acetate (50 ml). The solution was washed with water (40 ml), dried (MgSO$_4$) and concentrated in vacuo. The residue was re-dissolved in diethyl ether and re-concentrated in vacuo to give the compound of Example 3b (1.6 g) as a single enantiomer.

Experimental MH$^+$ 499.9; expected 500.1

$^1$H-NMR (CDCl$_3$): 1.98-2.00 (3H), 4.46-4.48 (1H), 4.79-4.81 (1H), 7.12-7.14 (1H), 7.81-7.86 (5H), 7.89-7.90 (1H) in vitro H.c. (L3) MED=1 μg/ml

Example 3c

Single Enantiomer

To a solution of the compound of Preparation 21 (2.5 g, 7.6 mmol) and 4-fluoro-3-(trifluoromethyl)benzonitrile (2.2 g, 11.4 mmol) in tetrahydrofuran (25 ml), at −10° C., was added dropwise potassium ten-butoxide (1M in tetrahydrofuran, 15.1 ml, 15.1 mmol). The reaction mixture was stirred at −10° C. for 2 h and then quenched by addition of saturated aqueous ammonium chloride solution (80 ml). The mixture was extracted with ethyl acetate (2×40 ml) and the combined extracts were washed with water (50 ml) and brine (40 ml), dried (MgSO$_4$) and concentrated in vacuo. The residue was purified by automated flash chromatography (Biotage™, 65M silica cartridge) with gradient elution, ethyl acetate:cyclohexane [0:100 to 50:50]. The appropriate fractions were combined and concentrated to give the title compound (3.1 g) as a single enantiomer.

Experimental MH$^+$ 499.9; expected 500.1

¹H-NMR (CDCl₃): 1.98-2.00 (3H), 4.48-4.50 (1H), 4.79-4.81 (1H), 7.13-7.15 (1H), 7.82-7.87 (5H), 7.88-7.90 (1H) in vitro H.c. (L3) MED>30 µg/ml Example 4

N-{1-Cyano-2-[4-cyano-2-fluoro-6-(trifluoromethyl)phenoxy]-1-methylethyl}-4-(pentafluorothio)benzamide

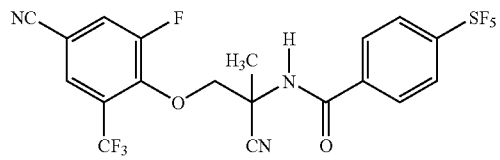

To a solution of the compound of Preparation 9 (500 mg, 1.5 mmol) and 3,4-difluoro-5-(trifluoromethyl)benzonitrile (376 mg, 1.8 mmol) in tetrahydrofuran (10 ml), at 0° C., was added dropwise potassium tert-butoxide (1M in tetrahydrofuran, 1.8 ml, 1.8 mmol). The reaction mixture was allowed to warm to room temperature and stirred for 18 h under nitrogen. The mixture was diluted with ethyl acetate (50 ml) and washed with saturated aqueous ammonium chloride solution (20 ml), water (20 ml) and brine (20 ml), dried (MgSO₄) and concentrated in vacuo. The residue was dissolved in acetonitrile (2 ml) and purified by automated preparative liquid chromatography (Gilson system, 150 mm×50 mm LUNA C18(2) 10 µm column, 120 ml/min) using an acetonitrile:water gradient [60:40 (for 13 min) to 98:2 (for 3 min) to 60:40 (for 1 min)]. The appropriate fractions were combined and concentrated to give the title compound (123 mg) as a racemic mixture.

Experimental MH⁺ 517.9; expected 518.1

1H-NMR (d₆-Acetone): 1.99-2.01 (3H), 4.90-4.92 (1H), 5.01-5.03 (1H), 7.99-8.03 (3H), 8.09-8.12 (3H) in vitro H.c. (L3) MED=3 µg/ml Similarly prepared were:

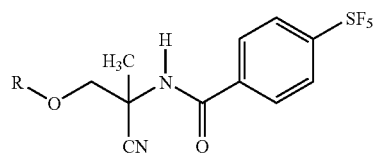

| Example No. | R | Precursor (all commercially available) | MH⁺ Found/ Expected | H.c. (L3) MED µg/ml |
|---|---|---|---|---|
| 5 | 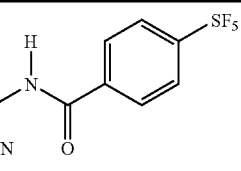 | 3-Chloro-4-fluorobenzonitrile | 465.9/ 466.0 | 3 |
| 6 | 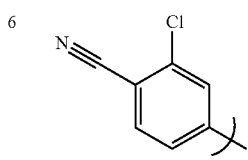 | 2-Chloro-4-fluorobenzonitrile | (M − H⁺)⁻ 464.0/ 464.0 | 3 |
| 7 | 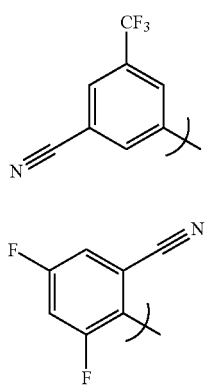 | 3-Fluoro-5-(trifluoromethyl)-benzonitrile | (M − H⁺)⁻ 498.0/ 498.1 | 30 |
| 8 | 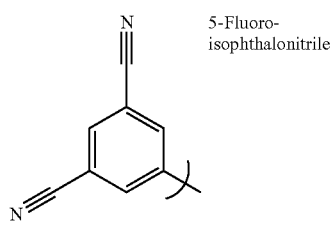 | 2,3,5-Trifluoro-benzonitrile | (M − H⁺)⁻ 465.5/ 466.0 | 30 |
| 9 | 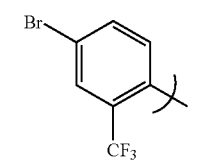 | 5-Fluoro-isophthalonitrile | (M − H⁺)⁻ 455.0/ 455.1 | 3 |
| 10 | 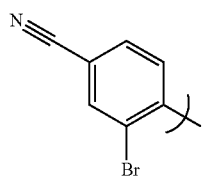 | 4-Bromo-1-fluoro-2-(trifluoromethyl)benzene | 552.9/ 553.0 | 10 |
| 11 | N≡C–C₆H₃(Br)– | 3-Bromo-4-fluorobenzonitrile | 509.9/ 510.0 | 3 |

Example 5

N-[2-(2-Chloro-4-cyanophenoxy)-1-cyano-1-methylethyl]-4-(pentafluorothio)benzamide ¹H-NMR (d₆-Acetone): 2.00-2.06 (3H), 4.72-4.76 (1H), 4.80-4.84 (1H), 7.40-7.42 (1H), 7.78-7.80 (1H), 7.87-7.89 (1H), 8.00-8.05 (2H), 8-08-8.12 (2H), 8.56-8.59 (1H)

Example 6

N-[2-(3-Chloro-4-cyanophenoxy)-1-cyano-1-methyl-ethyl]-4-(pentafluorothio)benzamide $^1$H-NMR (d$_6$-Acetone): 1.97-1.99 (3H), 4.60-4.63 (1H), 4.76-4.79 (1H), 7.20-7.22 (1H), 7.38-7.39 (1H), 7.80-7.82 (1H), 8.00-8.03 (2H), 8.08-8.11 (2H)

Example 7

N-{1-cyano-2-[3-cyano-5-(trifluoromethyl)phenoxy]-1-methylethyl}-4-(pentafluorothio)benzamide $^1$H-NMR (d$_6$-Acetone): 1.99-2.01 (3H), 4.65-4.68 (1H), 4.80-4.83 (1H), 7.75-7.77 (1H), 7.79-7.82 (2H), 7.99-8.02 (2H), 8.10-8.13 (2H)

Example 8

N-[1-Cyano-2-(2-cyano-4,6-difluorophenoxy)-1-methylethyl]-4-(pentafluorothio)benzamide $^1$H-NMR (d$_6$-Acetone): 2.01-2.04 (3H), 4.82-4.84 (2H), 7.47-7.50 (1H), 7.57-7.60 (1H), 7.99-8.03 (2H), 8.09-8.12 (2H)

Example 9

N-[1-Cyano-2-(3,6-dicyanophenoxy)-1-methyl-ethyl]-4-(pentafluorothio)benzamide $^1$H-NMR (d$_6$-Acetone): 1.98-2.00 (3H), 4.63-4.65 (1H), 4.78-4.81 (1H), 7.82-7.84 (2H), 7.89-7.90 (1H), 8.00-8.03 (2H), 8.09-8.12 (2H)

Example 10

N-{2-[4-Bromo-2-(trifluoromethyl)phenoxy]-1-cyano-1-methylethyl}-4-(pentafluorothio)benzamide $^1$H-NMR (d$_6$-Acetone): 1.98-2.01 (3H), 4.61-4.63 (1H), 4.74-4.77 (1H), 7.35-7.38 (1H), 7.78-7.82 (2H), 8.00-8.03 (2H), 8.06-8.09 (2H)

Example 11

N-[2-(2-Bromo-4-cyanophenoxy)-1-cyano-1-methyl-ethyl]-4-(pentafluorothio)benzamide $^1$H-NMR (CD$_3$OD): 1.95-1.98 (3H), 4.57-4.60 (1H), 465-4.68 (1H), 7.21-7.23 (1H), 7.70-7.72 (1H), 7.94-8.01 (5H)

Example 12

N-[1-Cyano-2-(2,4-dichlorophenoxy)-1-methyl-ethyl]-4-(pentafluorothio)benzamide

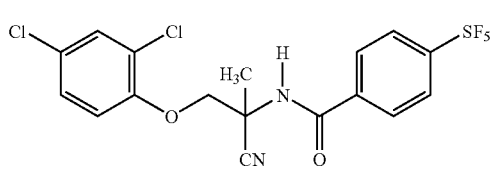

To a solution of the compound of Preparation 9 (120 mg, 0.4 mmol) in dimethyl sulphoxide (0.8 ml) was added 2,4-dichloro-1-fluorobenzene (90 mg, 0.5 mmol), followed by potassium ten-butoxide (1M in tetrahydrofuran, 0.5 ml, 0.5 mmol). The reaction mixture was then stirred at room temperature for 18 h. The reaction mixture was purified by automated preparative liquid chromatography (Gilson system, 150 mm×22.4 mm Gemini C18(2) 5 μm column, 20 ml/min) using an acetonitrile:water gradient [50:50 (for 2 min) to 98:2 (for 13 min) to 50:50 (for 2 min)]. The appropriate fractions were combined and concentrated in vacuo to give the title compound (55 mg).

Experimental MH$^+$ 474.9; expected 475.0

$^1$H-NMR (d$_6$-Acetone): 2.00-2.02 (3H), 4.59-4.61 (1H), 4.68-4.70 (1H), 720-7.22 (1H), 7.34-7.36 (1H), 8.00-8.02 (2H), 8.09-8.11 (2H) in vitro H.c. (L3) MED=3

Similarly prepared were:

| Example No. | R | Precursor (commercially available) unless stated | MH$^+$ Found/ Expected | H.c. (L3) MED μg/ml |
|---|---|---|---|---|
| 13a | F—⟨Cl⟩— | 2-chloro-1,4-difluorobenzene* | N/A | 1 |
| 13b | Cl, F—⟨⟩— | 2-chloro-1,4-difluorobenzene* | N/A | 1 |
| 14 | Cl—⟨CN⟩— | 3-Chloro-5-fluorobenzonitrile | (M − H$^+$)$^−$ 463.9/ 464.0 | 3 |
| 15 | Cl—⟨⟩— | 1-Chloro-4-fluorobenzene | 440.9/ 441.0 | 30 |
| 16 | Br—⟨CN⟩— | 4-Bromo-2-fluorobenzonitrile | 510.0/ 510.0 | 10 |

-continued

Structure: R-O-CH2-C(CH3)(CN)-NH-C(=O)-C6H4-SF5

| Example No. | R | Precursor (commercially available) unless stated | MH+ Found/ Expected | H.c. (L3) MED µg/ml |
|---|---|---|---|---|
| 17 | 5-chloro-2-cyanophenyl (Cl at 5, CN at 2) | 5-Chloro-2-fluorobenzonitrile | 465.9/ 466.0 | 3 |
| 18 | 2-fluoro-3-cyanophenyl | 2,6-Difluoro-benzonitrile | 449.9/ 450.1 | 10 |
| 19 | 2-cyanophenyl | 2-Fluoro-benzonitrile | 432.0/ 432.1 | 10 |
| 20 | 4-iodophenyl | 1-Fluoro-4-iodobenzene | (M − H+)− 531.0/ 531.0 | 3 |
| 21 | 2-(trifluoromethyl)phenyl | 1-Fluoro-2-(trifluoromethyl)benzene | 474.9/ 475.1 | 30 |
| 22 | 4-cyanophenyl | 4-Fluoro-benzonitrile | (M − H+)− 430.1/ 430.1 | 10 |
| 23 | 3,5-difluorophenyl-Cl | 1-Chloro-3,5-difluorobenzene | 459.0/ 459.0 | 30 |
| 24 | 4-chloro-2-cyanophenyl | 4-Chloro-2-fluorobenzonitrile | 465.9/ 466.0 | 3 |

-continued

| Example No. | R | Precursor (commercially available) unless stated | MH+ Found/ Expected | H.c. (L3) MED µg/ml |
|---|---|---|---|---|
| 25 | 2-chlorophenyl | 1-Chloro-2-fluorobenzene | 440.9/ 441.0 | 10 |
| 26 | 2-chloro-6-cyanophenyl | 2-Chloro-6-fluorobenzonitrile | 465.9/ 466.0 | 10 |
| 27a | 4-fluoro-2-cyanophenyl | 2,5-Difluoro-benzonitrile* | 449.9/ 450.1 | 3 |
| 27b | 2-fluoro-5-cyanophenyl | 2,5-Difluoro-benzonitrile* | 449.9/ 450.1 | 3 |
| 28 | 4-chloro-2-fluorophenyl | 4-Chloro-1,2-difluorobenzene | 459.0/ 459.0 | 3 |
| 29a | 3-fluoro-4-cyanophenyl | 3,4-Difluoro-benzonitrile* | 449.9/ 450.1 | 10 |
| 29b | 4-fluoro-3-cyanophenyl | 3,4-Difluoro-benzonitrile* | 449.9/ 450.1 | 10 |
| 30 | 2-fluoro-4-(trifluoromethyl)phenyl | 1,2-Difluoro-4-(trifluoromethyl)benzene | 493.0/ 493.1 | 10 |
| 31 | 3-chlorophenyl | 1-Chloro-3-fluorobenzene | 441.0/ 441.0 | 10 |

-continued

[Structure: R-O-CH2-C(CH3)(CN)-NH-C(=O)-C6H4-SF5]

| Example No. | R | Precursor (commercially available) unless stated | MH+ Found/ Expected | H.c. (L3) MED μg/ml |
|---|---|---|---|---|
| 32 | 4-cyano-2-bromophenyl (Br, CN substituted) | 4-Bromo-3-fluorobenzonitrile | 509.8/ 510.0 | 3 |
| 33a | 4-fluoro-2-bromophenyl | 2-Bromo-1,4-difluorobenzene* | (M − H+)− 500.9/ 501.0 | 10 |
| 33b | 2-fluoro-4-bromophenyl | 2-Bromo-1,4-difluorobenzene* | (M − H+)− 500.9/ 501.0 | 10 |
| 34 | 4-bromo-2-fluorophenyl | 4-Bromo-1,2-difluorobenzene | 502.9/ 503.0 | 10 |
| 35 | 3-bromo-5-cyanophenyl | 3-Bromo-5-fluorobenzonitrile | 509.9/ 510.0 | 3 |
| 36 | 2-cyano-3-(trifluoromethyl)phenyl | 3-Fluoro-2-(trifluoromethyl)benzonitrile | 500.1/ 500.1 | 10 |
| 37 | 2-cyano-3-bromophenyl | 2-Bromo-3-fluorobenzonitrile | 509.9/ 510.0 | 3 |
| 38 | 2,5-dichlorophenyl | 1,4-Dichloro-2-fluorobenzene | 474.9/ 475.0 | 10 |
| 39 | 2-chloro-3-fluorophenyl | 2-Chloro-1,3-difluorobenzene | 459.0/ 459.0 | 30 |
| 40 | 2-cyano-3-bromophenyl | 2-Bromo-6-fluorobenzonitrile | 509.8/ 510.0 | 10 |
| 41 | 5-bromo-2-cyanophenyl | 5-Bromo-2-fluorobenzonitrile | 509.9/ 510.0 | 10 |
| 42 | 2,3-dichlorophenyl | 1,2-Dichloro-3-fluorobenzene | 475.0/ 475.0 | 30 |

*Mixtures of regioisomers were obtained from these starting materials

Example 13

Example 13a

N-[2-(2-Chloro-4-fluorophenoxy)-1-cyano-1-methylethyl]-4-(pentafluorothio)benzamide and Example 13b N-[2-(3-Chloro-4-fluorophenoxy)-1-cyano-1-methylethyl]-4-(pentafluorothio)benzamide $^1$H-NMR (d$_6$-Acetone): 1.97-2.01 (3H), 4.58-4.61 (1H), 4.62-4.65 (1H), 7.09-7.12 (1H), 7.22-7.28 (2H), 7.99-8.02 (2H), 8.07-8.10 (2H) (for major component) 3:1 mixture of regioisomers

Example 14

N-[2-(3-Chloro-5-cyanophenoxy)-1-cyano-1-methylethyl]-4-(pentafluorothio)benzamide $^1$H-NMR (d$_6$-Acetone): 1.99-2.02 (3H), 4.58-4.61 (1H), 4.69-4.72 (1H), 7.43-7.47 (3H), 7.99-8.02 (2H), 8.08-8.11 (2H)

Example 15

N-[2-(4-Chlorophenoxy)-1-cyano-1-methylethyl]-(pentafluorothio)benzamide $^1$H-NMR (d$_6$-Acetone); 1.97-1.99 (3H), 4.42-4.44 (1H), 4.59-4.61 (1H), 7.02-7.05 (2H), 7.30-7.33 (2H), 7.99-8.01 (2H), 8.09-8.11 (2H)

Example 16

N-[2-(5-Bromo-2-cyanophenoxy)-1-cyano-1-methylethyl]-4-(pentafluorothio)benzamide $^1$H-NMR (CO$_3$OD): 1.90-1.93 (3H), 4.61-4.63 (2H), 7.30-7.33 (1H), 7.50-7.59 (2H), 7.95-7.98 (2H), 7.98-8.01 (2H)

Example 17

N-[2-(4-Chloro-2-cyanophenoxy)-1-cyano-1-methylethyl]-4-(pentafluorothio)benzamide $^1$H-NMR (d$_6$-Acetone): 2.00-2.02 (3H), 4.76-4.79 (2H), 7.38-7.41 (1H), 7.67-7.70 (1H), 7.74-7.77 (1H), 7.99-8.02 (2H), 8.09-8.11 (2H)

Example 18

N-[1-Cyano-2-(2-cyano-3-fluorophenoxy)-1-methylethyl]-4-(pentafluorothio)benzamide $^1$H-NMR (d$_6$-Acetone): 1.50-1.51 and 1.79-1.80 (3H), 4.79-4.80 (2H), 7.00-7.03 (1H), 7.19-7.21 (1H), 7.70-7.76 (1H), 8.00-8.04 (2H), 8.08-8.10 (1H), 8.17-8.19 (1H)

Example 19

N-[1-Cyano-2-(2-cyanophenoxy)-1-methylethyl]-4-(pentafluorothio)benzamide $^1$H-NMR (d$_6$-Acetone): 2.00-2.02 (3H), 4.76-4.78 (2H), 7.15-7.17 (1H), 7.36-7.38 (1H), 7.63-7.66 (2H), 7.99-8.01 (2H), 8.10-8.12 (2H)

Example 20

N-[1-Cyano-2-(4-iodophenoxy)-1-methylethyl]-4-(pentafluorothio)benzamide $^1$H-NMR (CDCl$_3$): 1.98-2.00 (3H), 4.26-4.28 (1H), 4.40-4.42 (1H), 6.71-6.73 (2H), 7.59-7.61 (2H), 7.81-7.83 (4H)

Example 21

N-{1-Cyano-1-methyl-2-[2-(trifluoromethyl)phenoxy]ethyl}-4-(pentafluorothio)benzamide $^1$H-NMR (CDCl$_3$): 1.98-2.00 (3H), 4.30-4.32 (1H), 4.63-4.65 (1H), 7.00-7.02 (1H), 7.11-7.13 (1H), 7.55-7.58 (1H), 7.60-7.62 (1H), 7.81-7.83 (4H)

Example 22

N-[1-Cyano-2-(4-cyanophenoxy)-1-methylethyl]-4-(pentafluorothio)benzamide $^1$H-NMR (d$_6$-Acetone); 1.97-2.00 (3H), 4.56-4.60 (1H), 4.68-4.72 (1H), 7.20-7.24 (2H), 7.75-7.79 (2H), 8.00-8.04 (2H), 8.07-8.11 (2H)

Example 23

N-[2-(3-Chloro-5-fluorophenoxy)-1-cyano-1-methylethyl]-4-(pentafluorothio)benzamide $^1$H-NMR (d$_6$-Acetone): 1.97-1.99 (3H), 4.50-4.52 (1H), 4.62-4.64 (1H), 6.82-6.85 (2H), 6.98-6.99 (1H), 8.00-8.02 (2H), 8.08-8.10 (2H)

Example 24

N-[2-(5-Chloro-2-cyanophenoxy)-1-cyano-1-methylethyl]4-(pentafluorothio)benzamide $^1$H-NMR (d$_6$-Acetone): 1.45-1.49 (3H), 4.79-4.82 (2H), 7.20-7.23 (1H), 7.45-7.47 (1H), 7.70-7.73 (1H), 8.00-8.03 (2H), 8.10-8.13 (2H)

Example 25

N-[2-(2-Chlorophenoxy)-1-cyano-1-methylethyl]-4-(pentafluorothio)benzamide $^1$H-NMR (d$_6$-Acetone): 2.00-2.02 (3H), 4.59-4.61 (1H), 4.63-4.65 (1H), 7.00-7.02 (1H), 7.20-7.22 (1H), 7.30-7.32 (1H), 7.41-7.43 (1H), 8.00-8.02 (2H), 8.10-8.13 (2H)

Example 26

N-[2-(3-Chloro-2-cyanophenoxy)-1-cyano-1-methylethyl]-4-(pentafluorothio)benzamide $^1$H-NMR (d$_6$-Acetone): 2.00-2.02 (3H), 4.79-4.82 (2H), 7.24-7.29 (2H), 7.65-7.68 (1H), 8.00-8.03 (2H), 8.08-8.10 (2H)

Example 27

Example 27a

N-[1-Cyano-2-(2-cyano-4-fluorophenoxy)-1-methylethyl]-4-(pentafluorothio)benzamide and Example 27b N-[1-Cyano-2-(3-cyano-4-fluorophenoxy)-1-methylethyl]-4-(pentafluorothio)benzamide $^1$H-NMR (d$_6$-Acetone): 2.00-2.02 (3H), 4.70-4.74 (2H), 7.39-7.42 (1H), 7.49-7.55 (1H), 7.57-7.60 (1H), 7.99-8.03 (2H), 8.10-8.14 (2H) (for major component) 4:1 mixture of regioisomers

Example 28

N-[2-(4-Chloro-2-fluorophenoxy)-1-cyano-1-methylethyl]-4-(pentafluorothio)benzamide $^1$H-NMR (d$_6$-Acetone): 1.97-1.99 (3H), 4.60-4.62 (1H), 4.69-4.71 (1H), 7.01-7.03 (1H), 7.19-7.22 (1H), 7.35-7.37 (1H), 7.99-8.01 (2H), 8.08-8.11 (2H)

Example 29

Example 29a

N-[1-Cyano-2-(4-cyano-2-fluorophenoxy)-1-methylethyl]-4-(pentafluorothio)benzamide and Example 29b N-[1-Cyano-2-(5-cyano-2-fluorophenoxy)-1-methylethyl]-4-(pentafluorothio)benzamide $^1$H-NMR (CDCl$_3$): 2.00-2.03 (3H), 4.45-4.48 (1H), 4.51-4.53 (1H), 7.07-7.11 (1H), 7.39-7.45 (2H), 7.80-7.84 (2H), 8.02-8.06 (2H) 1:1 mixture of regioisomers

Example 30

N-{1-Cyano-2-[2-fluoro-4-(trifluoromethyl)phenoxy]-1-methylethyl}-4-(pentafluorothio)benzamide $^1$H-NMR (d$_6$-Acetone): 1.99-202. (3H), 4.70-4.73 (1H), 4.77-4.80 (1H), 7.45-7.49 (1H), 7.52-7.57 (2H), 7.99-8.03 (2H), 8.03-8.06 (2H)

Example 31

N-[2-(3-Chlorophenoxy)-1-cyano-1-methylethyl]-4-pentafluorothio)benzamide $^1$H-NMR (d$_6$-Acetone): 1.96-1.99 (3H), 4.45-4.48 (1H), 4.60-4.63 (1H), 7.00-7.03 (2H), 7.09-7.11 (1H), 7.30-7.33 (1H), 8.00-8.03 (2H), 8.05-8.08 (2H)

Example 32

N-[2-(2-Bromo-5-cyanophenoxy)-1-cyano-1-methylethyl]-4-(pentafluorothio)benzamide $^1$H-NMR (CD$_3$OD): 1.96-2.00 (3H), 4.54-4.57 (1H), 4.60-4.63 (1H), 7.25-7.28 (1H), 7.44-7.46 (1H), 7.77-7.80 (1H), 7.95-8.05 (4H)

Example 33

Example 33a

N-[2-(2-Bromo-4-fluorophenoxy)-1-cyano-1-methylethyl]-4-(pentafluorothio)benzamide and Example 33b N-[2-(3-Bromo-4-fluorophenoxy)-1-cyano-1-methylethyl]-4-(pentafluorothio)benzamide $^1$H-NMR (CD$_3$OD): 1.96-1.98 (3H), 4.46-4.48 (1H), 4.53-4.55 (H), 7.09-7.13 (2H), 7.38-7.40 (1H), 7.92-8.00 (4H) (for major component) 3:1 mixture of regioisomers

Example 34

N-[2-(4-Bromo-2-fluorophenoxy)-1-cyano-1-methylethyl]-4-(pentafluorothio)benzamide $^1$H-NMR (CD$_3$OD): 1.90-1.92 (3H), 4.50-4.52 (1H), 4.52-4.54 (1H), 7.07-7.10 (1H), 7.11-7.13 (H), 7.36-7.38 (1H), 7.95-7.98 (4H)

Example 35

N-[2-(3-Bromo-5-cyanophenoxy)-1-cyano-1-methylethyl]-4-(pentafluorothio)benzamide $^1$H-NMR (CD$_3$OD): 1.95-1.97 (3H), 4.40-4.42 (1H), 4.58-4.60 (1H), 7.40-7.41 (1H), 7.56-7.58 (2H), 7.95-8.00 (4H)

Example 36

N-{1-Cyano-2-[3-cyano-2-(trifluoromethyl)phenoxy]-1-methylethyl}-4-(pentafluorothio)benzamide $^1$H-NMR (CD$_3$OD): 1.90-1.95 (3H), 4.57-4.61 (1H), 4.67-4.71 (1H), 7.55-7.58 (1H), 7.58-7.61 (1H), 7.72-7.76 (1H), 7.92-8.00 (4H)

Example 37

N-[2-(2-Bromo-3-cyanophenoxy)-1-cyano-1-methylethyl]-4-(pentafluorothio)benzamide $^1$H-NMR (d$_6$-Acetone): 2.01-2.03 (3H), 4.73-4.75 (1H), 4.77-4.79 (1H), 7.45-7.47 (1H), 7.53-7.60 (2H), 8.00-8.02 (2H), 8.09-8.11 (2H)

Example 38

N-[1-Cyano-2-(2,5-dichlorophenoxy)-1-methylethyl]-4-(pentafluorothio)benzamide $^1$H-NMR (CD$_3$OD): 1.96-1.97 (3H), 4.50-4.52 (1H), 4.57-4.59 (1H), 6.99-7.01 (1H), 7.19-7.20 (1H), 7.37-7.39 (1H), 7.92-8.00 (4H)

Example 39

N-[2-(2-Chloro-3-fluorophenoxy)-1-cyano-1-methylethyl]-4-(pentafluorothio)benzamide $^1$H-NMR (CD$_3$OD): 1.95-1.99 (3H), 4.50-4.54 (1H), 4.59-4.63 (1H), 6.85-6.89 (1H), 6.95-6.98 (1H), 7.22-7.27 (1H), 7.92-8.00 (4H)

Example 40

N-[2-(3-Bromo-2-cyanophenoxy)-1-cyano-1-methylethyl]-4-(pentafluorothio)benzamide $^1$H-NMR (d$_6$-Acetone): 2.00-2.02 (3H), 4.78-4.80 (2H), 7.38-7.41 (1H), 7.41-7.43 (1H), 7.60-7.63 (1H), 8.00-8.02 (2H), 8.10-8.12 (2H)

Example 41

N-[2-(4-Bromo-2-cyanophenoxy)-1-cyano-1-methylethyl]-4-(pentafluorothio)benzamide $^1$H-NMR (CD$_3$OD): 1.96-1.98 (3H), 4.61-4.63 (2H), 7.20-7.22 (1H), 7.75-7.78 (1H), 7.81-7.82 (1H), 7.90-7.93 (2H), 7.98-8.00 (2H)

Example 42

N-[1-Cyano-2-(2,3-dichlorophenoxy)-1-methylethyl]-4-(pentafluorothio)benzamide $^1$H-NMR (CD$_3$OD): 1.96-1.99 (3H), 4.50-4.53 (1H), 4.56-4.59 (1H), 7.08-7.10 (1H), 7.15-7.17 (1H), 7.20-7.23 (1H), 7.90-8.00 (4H)

Example 43

4-(2-Cyano-2-{[4-(pentafluorothio)benzoyl]amino}propoxy)-3-(trifluoromethyl)benzamide

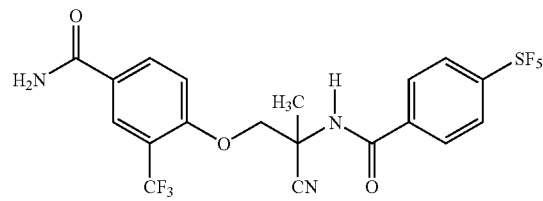

To a solution of the compound of Preparation 9 (200 mg, 0.6 mmol) in anhydrous dimethyl sulphoxide (3 ml) was added dropwise potassium tert-butoxide (1M in tetrahydrofuran, 1.2 ml, 1.2 mmol). After stirring for 15 min, 4-fluoro-3-(trifluoromethyl)benzamide (251 mg, 1.2 mmol) was added and the reaction mixture was stirred at room temperature for 4 h. Additional potassium tert-butoxide (1M in tetrahydrofuran, 1.2 ml, 1.2 mmol) was added and the reaction mixture was stirred for a further 18 h. The mixture was quenched by addition of aqueous ammonium chloride solution and extracted with ethyl acetate. The combined extracts were washed with water and brine, dried (MgSO$_4$) and concentrated in vacuo. The residue was purified by automated flash chromatography (Biotage™, 25+S silica cartridge) with gradient elution, ethyl acetate:cyclohexane [12:88 to 100:0]. The appropriate fractions were combined and concentrated give the title compound (290 mg) as a racemic mixture.

Experimental MH$^+$ 518.0; expected 518.1

$^1$H-NMR (CD$_3$OD): 1.95-1.98 (3H), 4.59-4.62 (1H), 4.69-4.72 (1H), 7.30-7.32 (1H), 7.92-8.00 (4H), 8.10-8.12 (1H), 8.12-8.13 (1H) in vitro H.c. (L3) MED=1

Example 44

N-{2-[2-Chloro-5-cyano-3-(trifluoromethyl)phenoxy]-1-cyano-1-methylethyl}-4-(pentafluorothio)benzamide

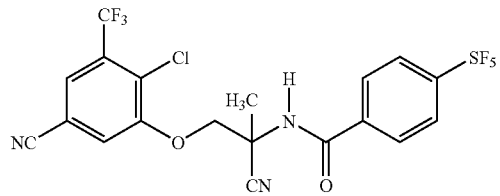

To a solution of the compound of Preparation 9 (110 mg, 0.3 mmol) and the compound of Preparation 14 (112 mg, 0.5 mmol) in anhydrous dimethyl sulphoxide (4 ml) was added dropwise potassium tert-butoxide (1M in tetrahydrofuran, 0.7 ml, 0.7 mmol). The reaction mixture was stirred at room temperature for 3 h and then quenched by addition of saturated aqueous ammonium chloride solution (15 ml). The mixture was extracted with ethyl acetate (2×5 ml) and the combined extracts were washed with water (5 ml) and brine (5 ml), dried (MgSO$_4$) and concentrated in vacuo. The residue was dissolved in acetonitrile:water (9:1, 2 ml) and purified by automated preparative liquid chromatography (Gilson system, 250 mm×50 mm LUNA C18(2) 10 μm column, 120 ml/min) using an acetonitrile:water gradient [65:35 (for 12 min) to 95:5 (for 3 min) to 65:35 (for 1 min)]. The appropriate fractions were combined and concentrated to give the title compound (28 mg) as a racemic mixture.

Experimental (M-H$^+$)$^-$ 532.0; expected 532.0

$^1$H-NMR (CD$_3$OD): 1.96-1.98 (3H), 4.60-4.62 (1H), 4.72-4.74 (1H), 7.80-7.81 (1H), 7.87-7.88 (1H), 7.92-8.00 (4H) in vitro H.c. (L3) MED=10

Similarly prepared were:

| Example No. | R | Precursor (commercially available unless stated) | MH$^+$ Found/ Expected | H.c. (L3) MED μg/ml |
|---|---|---|---|---|
| 45 | 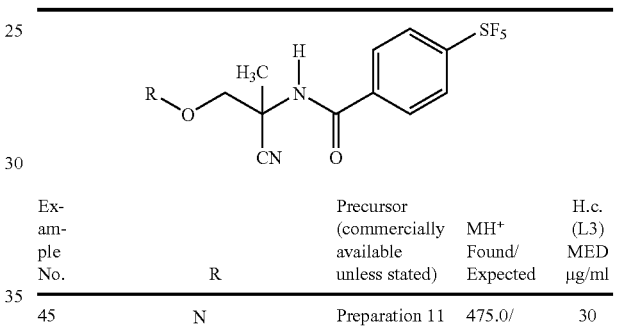 | Preparation 11 | 475.0/ 475.1 | 30 |
| 46 | 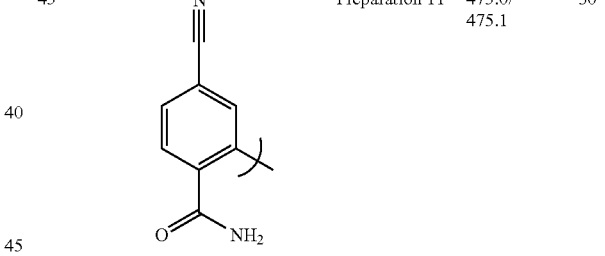 | Preparation 12 | 456.9/ 457.1 | 10 |
| 47 | 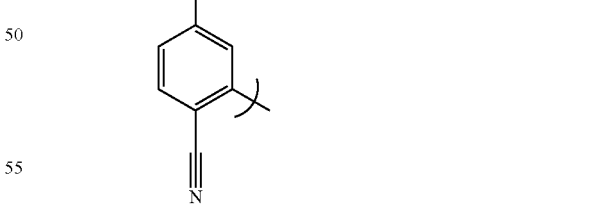 | Preparation 13 | (M − H$^+$)$^-$ 455.0/ 455.1 | 10 |

-continued

| Example No. | R | Precursor (commercially available unless stated) | MH+ Found/ Expected | H.c. (L3) MED µg/ml |
|---|---|---|---|---|
| 48 | (3-cyano-5-fluorophenyl) | 3,5-Difluoro-benzonitrile | 450.2/ 450.1 | 3 |
| 49 | (3-chloro-4-carbamoylphenyl) | 3-Chloro-4-fluoro-benzamide | 483.9/ 484.1 | 10 |

Example 45

4-Cyano-2-(2-cyano-2-{[4-(pentafluorothio)benzoyl]amino}propoxy)benzamide $^1$H-NMR (d$_6$-Acetone): 1.99-2.01 (3H) 4.78-4.81 (2H), 7.54-7.55 (1H), 7.69-7.70 (1H), 7.98-8.01 (3H), 8.12-8.14 (2H)

Example 46

N-[1-Cyano-2-(2,5-dicyanophenoxy)-1-methylethyl]-4-(pentafluorothio)benzamide $^1$H-NMR (CD$_3$OD) 1.96-1.98 (3H), 4.65-4.67 (1H), 4.70-4.72 (1H), 7.48-7.50 (1H), 7.69-7.70 (1H), 7.82-7.84 (1H), 7.95-7.97 (2H), 8.00-8.02 (2H)

Example 47

N-[1-Cyano-2-(2,4-dicyanophenoxy)-1-methylethyl]-4-(pentafluorothio)benzamide $^1$H-NMR (CDCl$_3$): 1.60-1.61 (3H), 4.50-4.52 (1H), 4.86-4.88 (1H), 7.15-7.17 (1H), 7.82-7.91 (6H)

Example 48

N-[1-Cyano-2-(3-cyano-5-fluorophenoxy)-1-methylethyl]-4-(pentafluorothio)benzamide $^1$H-NMR (CDCl$_3$): 1.97-1.99 (3H), 4.40-4.42 (1H), 4.44-4.46 (1H), 6.92-6.94 (1H), 7.00-7.02 (2H), 7.92-7.94 (4H)

Example 49

3-Chloro-4-(2-cyano-2-{[4-(pentafluorothio)benzoylamino)benzoyl]amino}propoxy)benzamide $^1$H-NMR (CDCl$_3$): 2.00-2.02 (3H), 4.39-4.41 (1H), 4.62-4.64 (1H), 7.00-7.02 (1H), 7.66-7.68 (1H), 7.83-7.88 (5H)

Example 50

N-[1-Cyano-2-(3-cyanophenoxy)-1-methylethyl]-4-(pentafluorothio)benzamide

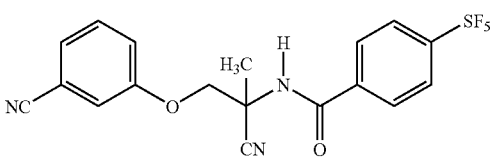

To a solution of the compound of Preparation 9 (200 mg, 0.6 mmol) in N,N-dimethylformamide (2 ml) was added sodium hydride (60% in oil, 0.32 mg, 1.3 mmol) and the mixture was stirred for 15 min. To the mixture was added 3-fluorobenzonitrile (81 mg, 0.7 mmol) in N,N-dimethylformamide (1 ml) and the reaction mixture was stirred at room temperature for 24 h. Additional sodium hydride (60% in oil, 64 mg, 2.7 mmol) was added and the mixture was stirred for a further 4 days. The mixture was quenched by addition of water and extracted with ethyl acetate. The combined extracts were washed with water and brine, dried (MgSO$_4$) and concentrated in vacuo. The residue was dissolved in dimethyl sulphoxide (2.8 ml) and purified by automated preparative liquid chromatography (Gilson system, 150 mm×50 mm LUNA C18(2) 10 µm column, 120 ml/min) using an acetonitrile:water gradient [55:45 (for 15 min) to 98:2 (for 3 min) to 55:45 (for 1 min)]. The appropriate fractions were combined and concentrated to give the title compound (46 mg) as a racemic mixture.

Experimental MH$^+$ 431.9, expected 432.1

$^1$H-NMR (d$_6$-Acetone): 1.98-2.00 (3H), 4.56-4.58 (1H), 4.67-4.69 (1H), 7.39-7.41 (2H), 7.43-7.44 (1H), 7.54-7.56 (1H), 8.00-8.02 (2H), 8.09-8.11 (2H) in vitro H.c. (L3) MED=3

Similarly prepared were:

| Example No. | R | Precursor (commercially available unless stated) | MH+ Found/ Expected | H.c. (L3) MED µg/ml |
|---|---|---|---|---|
| 51 | (3-cyano-5-fluorophenyl with F) | 3,4,5-Trifluoro-benzonitrile | (M − H$^+$)$^-$ 465.6/ 466.0 | 3 |
| 52 | (2-chloro-6-trifluoromethylphenyl) | 1-Chloro-3-fluoro-2-(trifluoromethyl)benzene | 508.7/ 509.0 | 10 |

Example 51

N-[1-Cyano-2-(4-cyano-2,6-difluorophenoxy)-1-methylethyl]-4-(pentafluorothio)benzamide $^1$H-NMR (d$_6$-Acetone): 1.98-2.00 (3H), 4.81-4.83 (1H), 4.85-4.87 (1H), 7.61-7.63 (2H), 8.00-8.03 (2H), 8.06-8.09 (2H)

Example 52

N-{2-[3-Chloro-2-(trifluoromethyl)phenoxy]-1-cyano-1-methylethyl}-4-(pentafluorothio)benzamide $^1$H-NMR (CD$_3$OD): 1.90-1.92 (3H), 4.50-4.52 (1H), 4.61-4.63 (1H), 718-7.20 (2H), 7.49-7.52 (1H), 7.95-8.00 (4H)

Example 53

3-Cyano-5-(2-cyano-2-{[4-(pentafluorothio)benzoyl]amino}propoxy)benzamide

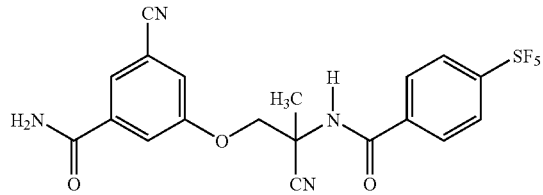

To a solution of the compound of Preparation 17 (194 mg, 0.4 mmol) in acetonitrile (4 ml) was added 1,1'-carbonyldiimidazole (99 mg, 0.6 mmol) and the reaction mixture was stirred at room temperature, under nitrogen, for 1.5 h. Additional 1,1'-carbonyldiimidazole (99 mg, 0.6 mmol) was added and the reaction mixture was stirred for a further 1 h. To the mixture was added aqueous ammonium hydroxide solution (35%, 5 ml) and the reaction mixture was stirred for 1 h. The mixture was quenched with water and diluted with ethyl acetate. The two layers were separated and the aqueous phase was extracted with ethyl acetate. The combined organic phases were washed with water and brine, dried (MgSO$_4$) and concentrated in vacuo. The residue was dissolved in methanol (1.5 ml), containing a few drops of dimethyl sulphoxide, and purified by automated preparative liquid chromatography (Gilson system, 150 mm×30 mm LUNA C18(2) 10 µm column, 40 ml/min) using an acetonitrile:water gradient [45:55 (for 14 min) to 98:2 (for 3 min) to 45:55 (for 1 min)]. The appropriate fractions were combined and concentrated to give the title compound (71 mg) as a racemic mixture.

Experimental (M-H$^+$) 473.0; expected 473.1

$^1$H-NMR (CD$_3$OD): 1.89-1.93 (3H), 4.45-4.48 (1H), 4.60-4.63 (1H), 7.56-7.58 (1H), 7.79-7.84 (2H), 7.90-8.00 (4H)

in vitro H.c. (L3) MED=30

PREPARATIONS

The following Preparations illustrate the synthesis of certain intermediates used in the preparation of the preceding Examples.

Preparation 1

3-(2-Amino-2-cyanopropoxy)-4-(trifluoromethyl)benzonitrile

A mixture of the compound of Preparation 6 (3.5 g, 14.4 mmol), ammonium chloride (1.2 g, 22.3 mmol) and ammonia (7N in methanol, 41.1 ml, 288.0 mmol) was stirred at room temperature for 20 min, before addition of sodium cyanide (921 mg, 18.4 mmol). The reaction mixture was stirred at room temperature for 65 h and then quenched by addition of aqueous sodium hydroxide solution (2M, 100 ml). The mixture was extracted with toluene (3×75 ml) and the combined extracts were washed with brine (100 ml), dried (MgSO$_4$) and concentrated in vacuo. To the residue was added dichloromethane (380 ml) and Amberlyst® 15 ion-exchange resin (prepared according to J. Org. Chem., 1998, 63, 3471). The solution was shaken gently for 17 h and the resin was removed and washed with cyclohexane, followed by tetrahydrofuran and methanol. To the resin was added ammonia (2M in methanol, 380 ml) and the solution was shaken for 1 h. To the solution was added tetrahydrofuran (380 ml) and the resin was removed. The solution was then concentrated in vacuo to give the title compound (3.2 g).

$^1$H-NMR (CDCl$_3$): 1.61-1.62 (3H), 3.97-4.00 (1H), 4.18-4.20 (1H), 7.20-7.22 (1H), 7.40-7.42 (1H), 7.73-7.75 (1H)

Preparation 2

4-(Pentafluorothio)benzoyl chloride

A solution of the compound of Preparation 3 (8.5 g, 34.3 mmol) in thionyl chloride (50 ml) was heated at 65° C. for 4 h. The mixture was concentrated in vacuo and the residue was triturated with toluene to give the title compound (7.6 g).

$^1$H-NMR (CDCl$_3$): 7.95-8.00 (2H), 8.21-8.26 (2H)

Preparation 3

4-(Pentafluorothio)benzoic acid

A mixture of the compound of Preparation 4 (8.0 g, 34.8 mmol) and sodium periodate (30.5 g, 142.0 mmol) in acetonitrile (60 ml), carbon tetrachloride (60 ml) and water (60 ml) was de-gassed and treated with ruthenium (III) chloride hydrate (157 mg, 0.7 mmol). The reaction mixture was stirred at room temperature for 1 h and then partitioned between diethyl ether and water. The two layers were separated and the organic phase was washed with aqueous sodium hydroxide solution (1N). The aqueous phase was adjusted to pH 1 by addition of hydrochloric acid and then extracted with diethyl ether. The combined extracts were washed with brine, dried (MgSO$_4$) and concentrated in vacuo to give the title compound (2.8 g).

Experimental (M-H$^+$)$^-$ 247.1; expected 247.0

Preparation 4

1-(Pentafluorothio)-4-vinylbenzene

A mixture of the compound of Preparation 5 (16.6 g, 50.4 mmol), tributyl(vinyl)tin (22.1 ml, 24.0 g, 75.6 mmol) and tetrakis(triphenylphosphine)palladium(0) (2.1 g, 1.8 mmol) in N,N-dimethylformamide (170 ml) was purged with nitrogen and heated at 100° C. for 1.5 h. The mixture was partitioned between diethyl ether and water and the organic phase was separated, washed with aqueous potassium fluoride solution (2×50 ml) and brine, dried (MgSO$_4$) and concentrated in vacuo. The residue was purified by column chromatography (silica, 800 g), eluting with pentane. The residue was further purified by distillation to give the title compound (18.0 g).

$^1$H-NMR (CDCl$_3$): 5.39-5.43 (1H), 5.80-5.84 (1H), 6.65-6.70 (1H), 7.41-7.44 (2H), 7.68-7.72 (2H)

Preparation 5

1-Iodo-4-(pentafluorothio)benzene

To a solution of 4-(pentafluorothio)aniline (15.0 g, 68.4 mmol) and ice (40.0 g) in hydrochloric acid (12M, 30 ml) was added a solution of sodium nitrite (5.0 g, 72.5 mmol) in water (120 ml) at 0° C. After stirring for 2 min, the mixture was added to potassium iodide (13.0 g, 78.3 mmol) in water (120 ml), ensuring the temperature did not rise above 10° C. The reaction mixture was stirred at 0° C. for 10 min and then at room temperature for 60 h. The mixture was extracted with diethyl ether (2×100 ml) and the combined extracts were washed with brine, dried (MgSO$_4$) and concentrated in vacuo. The residue was purified by column chromatography (silica, 300 g), eluting with diethyl ether:cyclohexane [1:10]. The appropriate fractions were combined and concentrated to give the title compound (16.6 g).

$^1$H-NMR (CDCl$_3$): 7.90-7.95 (2H), 8.20-8.25 (2H)

Preparation 6

3-(2-Oxopropoxy)-4-(trifluoromethyl)benzonitrile

A solution of the compound of Preparation 7 (7.0 g, 24.5 mmol) in acetone (122 ml) and hydrochloric acid (2M, 61.1 ml) was heated at reflux for 19 h. After cooling to room temperature, the mixture was concentrated in vacuo and to the residue was added ethyl acetate (150 ml). The solution was washed with saturated aqueous sodium carbonate solution and water, dried (MgSO$_4$) and concentrated in vacuo.

The residue was re-crystallised from cyclohexane:tert-butyl ether [95:5] to give the title compound (3.5 g).

$^1$H-NMR (CDCl$_3$): 2.37-2.39 (3H), 4.60-4.62 (2H), 7.07-7.09 (1H), 7.39-7.41 (1H), 7.75-7.78 (1H)

Preparation 7

3-[(Methyl-1,3-dioxolan-2-yl)methoxy]-4-(trifluoromethyl)benzonitrile

To a mixture of 3-fluoro-4-(trifluoromethyl)benzonitrile (12.1 g, 63.9 mmol) and the compound of Preparation 8 (21.0 g, 160.0 mmol) in tetrahydrofuran (345 ml), at 0° C. and under nitrogen, was added dropwise potassium tert-butoxide (1M in tetrahydrofuran, 70.3 ml, 70.3 mmol). The reaction mixture was stirred at 0° C. for 1 h and then allowed to warm to room temperature. To the mixture was added ethyl acetate (200 ml) and saturated aqueous ammonium chloride solution (250 ml) and the two layers were separated. The organic phase was washed with saturated aqueous ammonium chloride solution, water and brine, dried (MgSO$_4$) and concentrated in vacuo. To the residue was added cyclohexane (100 ml) and the mixture was allowed to stand for 1 h. The solid residue was collected by filtration and dried to give the title compound (16.3 g).

$^1$H-NMR (CDCl$_3$): 1.45-1.47 (3H), 4.00-4.06 (6H), 7.20-7.21 (1H), 7.32-7.34 (1H), 7.63-7.65 (1H)

Preparation 8

(2-Methyl-1,3-dioxolan-2-yl)methanol

To a solution of 1,2-bis(trimethylsilyloxy)ethane (41.2 g, 200.0 mmol) and 1-hydroxyacetone (15.2 ml, 200.0 mmol) in anhydrous tetrahydrofuran (35 ml) was added dropwise trimethylsilyl trifluoromethanesulphonate (2.0 ml, 11.1 mmol). The reaction mixture was stirred at room temperature for 18 h, before addition of pyridine (32.3 ml). The mixture was poured into aqueous sodium hydrogen carbonate solution (100 ml) and extracted with ethyl acetate (3×150 ml). The combined extracts were washed with brine, dried (MgSO$_4$) and concentrated in vacuo. The residue was azeotroped with toluene (×2) to give the title compound (16.6 g).

$^1$H-NMR (CDCl$_3$): 1.35-1.37 (3H), 3.51-3.53 (2H), 3.98-4.00 (4H)

Preparation 9

N-(1-Cyano-2-hydroxy-1-methylethyl)-4-(pentafluorothio)benzamide

To a solution of the compound of Preparation 10 (563 mg, 5.6 mmol) and N,N-diisopropylethylamine (1.1 ml, 6.4 mmol) in tetrahydrofuran (9 ml), at −10° C., was added dropwise the compound of Preparation 2 (1.5 g, 5.6 mmol) in tetrahydrofuran (10 ml). After stirring for 1 h, the reaction mixture was concentrated in vacuo and to the residue was added ethyl acetate (200 ml). This solution was washed with hydrochloric acid (0.1M, 80 ml), saturated aqueous sodium hydrogen carbonate solution (100 ml) and brine (50 ml), dried (MgSO$_4$) and concentrated in vacuo to give the title compound (1.6 g)

Experimental (M-H$^+$)$^-$ 329.1; expected 329.0

Preparation 10

2-Amino-3-hydroxy-2-methylpropanenitrile

A mixture of sodium cyanide (13.0 g, 259.0 mmol), ammonium chloride (16.8 g, 314.0 mmol) and ammonia (7M in methanol, 579 ml, 4.1 mol) was stirred at room temperature for 10 min, before addition of 1-hydroxyacetone (14 ml, 202.0 mmol). The reaction mixture was stirred at room temperature, under nitrogen, for 23 h and then concentrated in vacuo. To the residue was added ethyl acetate (200 ml) and the mixture was filtered. The filtrate was concentrated in vacuo and to the residue was added dichloromethane. The solution was cooled to −20° C. and allowed to stand for 60 h. The resulting precipitate was collected by filtration, washed with cold dichloromethane and dried in vacuo to give the title compound (8.3 g).

$^1$H-NMR (CD$_3$OD): 1.40-1.43 (3H), 3.45-3.55 (2H)

Preparation 11

4-Cyano-2-fluorobenzamide

To a solution of 4-cyano-2-fluorobenzoic acid (500 mg, 3.0 mmol) in acetonitrile (20 ml) was added 1,1'-carbonyldiimidazole (736 mg, 4.5 mmol). The mixture was stirred at room temperature for 45 min, before addition of aqueous ammonium hydroxide solution (35%, 10 ml). The reaction mixture was stirred for 45 min and ice cold water (15 ml) was added. The precipitate was collected by filtration and dried in a vacuum oven at 60° C. for 18 h to give the title compound (292 mg).

$^1$H-NMR (d$_6$-Acetone): 7.70-7.78 (2H), 7.98-8.02 (1H)

Preparation 12

2-Fluoroterephthalonitrile

To a solution of the compound of Preparation 11 (138 mg, 0.8 mmol) in acetonitrile (6 ml) and water (2 ml) was added palladium (II) chloride (15 mg) and the reaction mixture was heated at 50° C. for 24 h. The mixture was concentrated in vacuo and the residue was extracted with ethyl acetate (2×10 ml). The combined extracts were dried (MgSO$_4$) and concentrated in vacuo to give the title compound (113 mg).
$^1$H-NMR (CD$_3$OD): 7.80-7.84 (2H), 7.84-7.87 (1H)

Preparation 13

4-Fluoroisophthalonitrile

To a solution of 2-fluoro-5-formylbenzonitrile (5.1 g, 33.9 mmol) in water (75 ml) was added hydroxylamine-O-sulphonic acid (4.6 g, 40.7 mmol) and the reaction mixture was heated at 50° C. for 5 h. The mixture was filtered and the solid material was washed with water and dried in vacuo for 18 h to give the title compound (4.3 g)
$^1$H-NMR (CDCl$_3$): 7.38-7.41 (1H), 7.91-7.94 (1H), 7.94-7.97 (1H)

Preparation 14

4-Chloro-3-fluoro-5-(trifluoromethyl)benzonitrile

A mixture of the compound of Preparation 15 (200 mg, 1.0 mmol), tert-butyl nitrite (0.2 ml, 1.5 mmol) and copper (II) chloride (209 mg, 1.2 mmol) in acetonitrile (10 ml) was heated at 70° C. for 2 h. The mixture was cooled and added to hydrochloric acid (20%, 10 ml), before addition of water (10 ml). The mixture was extracted with dichloromethane (2×10 ml) and the combined organic phases were dried (MgSO$_4$) and concentrated in vacuo to give the title compound (180 mg).
$^1$H-NMR (CDCl$_3$): 7.63-7.67 (1H), 7.80-7.82 (1H)

Preparation 15

4-Amino-3-fluoro-5-(trifluoromethyl)benzonitrile

A mixture of the compound of Preparation 16 (1.1 g, 4.3 mmol), sodium cyanide (418 mg, 8.5 mmol) and nickel (II) bromide (932 mg, 4.3 mmol) in 1-methyl-2-pyrrolidinone (12 ml) was heated at 160° C. in a microwave oven (CEM 300W) for 6 h. To the mixture was added water (60 ml) and dichloromethane (50 ml) and the solution was filtered through Arbocel®, washing through with dichloromethane (50 ml). The two layers were separated and the organic phase was dried (MgSO$_4$) and concentrated in vacuo. The residue was combined with other crude batches (approximately 4 g in total) and purified by automated flash chromatography (Biotage™ 60si cartridge) with gradient elution, ethyl acetate:cyclohexane [0:1 to 2:3]. The appropriate fractions were combined and concentrated to give the title compound (1.7 g).
$^1$H-NMR (CDCl$_3$): 4.75-4.90 (2H), 7.39-7.43 (1H), 7.56-7.58 (1H)

Preparation 16

4-Bromo-2-fluoro-6-(trifluoromethyl)aniline

To a solution of 2-amino-3-fluorobenzotrifluoride (0.7 ml, 5.6 mmol) in acetonitrile (2 ml) was added N-bromosuccinimide (994 mg, 5.6 mmol), followed by iron (III) chloride (90.1 mg, 0.6 mmol). The reaction mixture was stirred at room temperature for 90 min, before addition of water (20 ml). The mixture was extracted with tert-butyl methyl ether (2×15 ml) and the combined extracts were washed with brine (20 ml), dried (MgSO$_4$) and concentrated in vacuo to give the title compound (1.4 g), which was used directly.

Preparation 17

3-Cyano-5-(2-cyano-2-{[4-(pentafluorothio)benzoyl]amino}propoxy)benzoic acid

To a solution of the compound of Preparation 18 (257 mg, 0.5 mmol) in tetrahydrofuran and water (1:1, 6 ml) was added lithium hydroxide monohydrate (44 mg, 1.0 mmol) and the reaction mixture was stirred at room temperature for 2 h. The mixture was adjusted to pH 4 by addition of hydrochloric acid (2M) and extracted with ethyl acetate. The combined organic phases were washed with brine, dried (MgSO$_4$) and concentrated in vacuo to give the title compound (202 mg).
Experimental MH$^+$ 475.8; expected 476.1

Preparation 18

Methyl-3-cyano-5-(2-cyano-2-{[4-(Pentafluorothio benzoyl]-amino}propoxy)benzoate To a solution of the compound of Preparation 9 (200 mg, 0.6 mmol) in anhydrous N,N-dimethylformamide (3 ml), at 0° C. and under nitrogen, was added sodium hydride (60% in oil, 48 mg, 1.2 mmol). After stirring for 15 min, a solution of the compound of Preparation 19 (217 mg, 1.2 mmol) in anhydrous N,N-dimethylformamide (1 ml) was added and the reaction mixture was stirred at room temperature for 2.5 h. The mixture was quenched by addition of water (10 ml) and additional water (10 ml) and ethyl acetate (20 ml) were added. The two layers were separated and the aqueous phase was extracted with ethyl acetate (2×20 ml). The combined extracts were washed with water and brine, dried (MgSO$_4$) and concentrated in vacuo. The residue was dissolved in dichloromethane and purified by automated flash chromatography (Biotage™ 25+M cartridge) with gradient elution, ethyl acetate:cyclohexane [6:94 to 50:50]. The appropriate fractions were combined and concentrated to give the title compound (61 mg).
$^1$H-NMR (CD$_3$OD): 1.96-1.98 (3H), 3.92-3.94 (3H), 4.50-4.52 (1H), 4.61-4.63 (1H), 7.63-7.64 (1H), 7.89-7.90 (1H), 7.94-7.97 (3H), 7.97-8.00 (2H)

Preparation 19

Methyl 3-cyano-5-fluorobenzoate

To a solution of 3-cyano-5-fluorobenzoic acid (1.0 g, 6.1 mmol) in dichloromethane (5 ml) and methanol (0.5 ml), at 0° C., was added dropwise (trimethylsilyl)diazomethane (2M in hexanes, 3.6 ml, 7.3 mmol). The reaction mixture was stirred at room temperature, under nitrogen, for 18 h and then concentrated in vacuo to give the title compound (1.1 g).
$^1$H-NMR (CDCl$_3$): 3.98-4.00 (3H), 7.56-7.58 (1H), 7.97-7.99 (1H), 8.15-8.17 (1H)

Preparation 20

(1-Cyano-2-hydroxy-1-methylethyl)-4-(pentafluorothio)benzamide

First-Eluting Enantiomer

The compound of Preparation 9 (12.1 g, 36.8 mmol) was dissolved in ethanol (4.5 ml) in batches of 605 mg and the enantiomers were separated by automated preparative liquid chromatography (Gilson system, 500×50 mm ID Chiralcel AD-H, 5 μm column, 50 m/min) using methanol:ethanol:hexane [10:10:80] as the mobile phase. The fractions containing the first eluting enantiomer were combined and concentrated to give the title compound (5.9 g).

Retention time=7.55 min 250×4.6 mm Chiralpak AD-H, 5 μm column, methanol:ethanol:hexane [10:10:80], 1 ml/min Experimental MH+ 331.0; expected 331.1

Preparation 21

N-(1-Cyano-2-hydroxy-1-methylethyl)-4-pentafluorothio)benzamide

Second-Eluting Enantiomer

The compound of Preparation 9 (12.1 g, 36.8 mmol) was dissolved in ethanol (4.5 ml) in batches of 605 mg and the enantiomers were separated by automated preparative liquid chromatography (Gilson system, 500×50 mm ID Chiralcel AD-H, 5 μm column, 50 ml/min) using methanol:ethanol:hexane [10:10:80] as the mobile phase. The fractions containing the second eluting enantiomer were combined and concentrated to give the title compound (5.7 g).

Retention time=10.40 min 250×4.6 mm Chiralpak AD-H, 5 μm column, methanol:ethanol:hexane [10:10:80], 1 ml/min Experimental MH+ 331.0; expected 331.1

The invention claimed is:

1. A compound of the formula

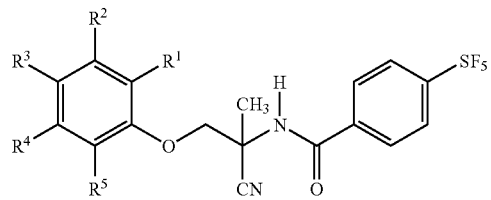

(I)

or a pharmaceutically acceptable salt of said compound, wherein:
$R^1$, $R^2$, $R^3$, $R^4$ and $R^5$ are each independently selected from H, halo, CN, $CF_3$ and $CONH_2$.

2. A compound according to claim 1 wherein $R^1$, $R^2$, $R^3$, $R^4$ and $R^5$ are each independently selected from H, F, Cl, Br, CN and $CF_3$.

3. A compound according to claim 2 wherein at least one of $R^1$, $R^2$, $R^3$, $R^4$ and $R^5$ is CN and at least two of $R^1$, $R^2$, $R^3$, $R^4$ and $R^5$ are H.

4. A compound according to claim 2 wherein $R^1$ and $R^4$ are H, one of $R^2$ and $R^3$ is H and the other is CN, and $R^5$ is selected from F, Cl, Br and $CF_3$.

5. A compound according to claim 4 wherein $R^3$ is CN and $R^5$ is $CF_3$.

6. A compound according to claim 1 selected from:
N-{1-cyano-2-[5-cyano-2-(trifluoromethyl)phenoxy]-1-methylethyl}-4-pentafluorothiobenzamide,
N-{(1R)-1-cyano-2-[5-cyano-2-(trifluoromethyl)phenoxy]-1-methylethyl}-4-pentafluorothiobenzamide,
N-{(1S)-cyano-2-[5-cyano-2-(trifluoromethyl)phenoxy]-1-methylethyl}-4-pentafluorothiobenzamide,
N-[2-(2-chloro-5-cyanophenoxy)-1-cyano-1-methylethyl]-4-pentafluorothiobenzamide,
N-[2-(2-chloro-5-cyanophenoxy)-(1R)-1-cyano-1-methylethyl]-4-pentafluorothiobenzamide,
N-[2-(2-chloro-5-cyanophenoxy)-(1S)-1-cyano-1-methylethyl]-4-penrafluorothiobenzamide,
N-{1-cyano-2-[4-cyano-2-(trifluoromethyl)phenoxy]-1-methyl ethyl}-4-pentafluorothiobenzamide,
N-{(1R)1-cyano-2-[4-cyano-2-(trifluoromethyl)phenoxy]-1-methylethyl}-4-pentafluorothiobenzamide,
N-{(1S)1-cyano-2-[4-cyano-2-(trifluoromethyl)phenoxy]-1-methylethyl}-4-pentafluorothiobenzamide,
N-{2-[2-chloro-5-cyano-3-(trifluoromethyl)phenoxy]-1-cyano-1-methylethyl}-4-pentafluorothiobenzamide,
N-{2-[2-chloro-5-cyano-3-(trifluoromethyl)phenoxy]-(1R)-1-cyano-1-methylethyl}-4-pentafluorothiobenzamide,
N-{2-[2-chloro-5-cyano-3-(trifluoromethyl)phenoxy]-(1S)-1-cyano-1-methylethyl}-4-pentafluorothiobenzamide,
N-[2-(2-chloro-4,5-dicyanophenoxy)-1-cyano-1-methylethyl]-4-pentafluorothiobenzamide,
N-[2-(2-chloro-4,5-dicyanophenoxy)-(1R)-1-cyano-1-methylethyl]-4-pentafluorothiobenzamide,
N-[2-(2-chloro-4,5-dicyanophenoxy)-(1S)-1-cyano-1-methylethyl]-4-pentafluorothiobenzamide,
N-{(1-cyano-2-[4-cyano-2-(trifluoromethyl)phenoxy]-1-methylethyl }-4-pentafluorothiobenzamide,
N-{(1R)-1-cyano-2-[4-cyano-2-(trifluoromethyl)phenoxy]-1-methylethyl}-4-pentafluorothiobenzamide, and
N-{(1S)-1-cyano-2-[4-cyano-2-(trifluoromethyl)phenoxy]-1-methylethyl}-4-pentafluorothiobenzamide,
or a pharmaceutically acceptable salt thereof 7. A pharmaceutical composition comprising a compound of formula (I) of claim 1, or a pharmaceutically acceptable salt thereof, and a pharmaceutically acceptable carrier.

8. The pharmaceutical composition according to claim 7 further comprising a second therapeutic agent.

9. The pharmaceutical composition according to claim 8 wherein the second therapeutic agent is selected from ivermectin, avermectin, abamectin, emamectin, eprinomectin, doramectin, selamectin, moxidectin, nemadectin, milbemycin oxime, albendazole, cambendazole, fenbendazole, flubendazole, mebendazole, oxfendazole, oxibendazole, parbendazole, tetramisole, levamisole, pyrantel pamoate, oxantel, morantel, closantel, triclabendazole, clorsulon, rafoxanide, niclosamide, praziquantel, epsiprantel, 2-desoxoparaherquamide, tipronil, pyriprole, pyrafluprole, lufenuron, spiromesifen, tebufenozide, spinosad, spinetoram, imidacloprid, dinotefuran, metaflumizone, thibendiamide, chlorantraniliprole, indoxacarb, pyridalyl, pyrimidifen and pyrifluquinazon.

10. A method of treatment of a parasitic infestation in a host animal, comprising treating said host animal with an effective amount of a compound of formula (I), or with a pharmaceutically acceptable salt or composition thereof, as defined in claim 1.

11. The method according to claim 10 wherein the host animal is a non-human animal.

12. The method according to claim 10 wherein the parasite is a nematode.

* * * * *